United States Patent [19]

Eidenschink et al.

[11] Patent Number: 4,882,082
[45] Date of Patent: Nov. 21, 1989

[54] NITROGEN-CONTAINING HETERCYCLIC COMPOUNDS

[75] Inventors: Rudolf Eidenschink, Kornblumenstr.; Joachim Krause, Dieburg; Reinhard Hittich, Modautal; Eike Poetsch, Muehltal; Bernhard Scheuble, Alsbach; Georg Weber, Erzhausen; Ludwig Pohl, Darmstadt, all of Fed. Rep. of Germany

[73] Assignee: Merck Patent Gesellschaft Mit Beschränkter Haftung, Darmstadt, Fed. Rep. of Germany

[21] Appl. No.: 172,424
[22] Filed: Mar. 23, 1988

Related U.S. Application Data

[60] Division of Ser. No. 884,349, Jul. 11, 1986, Pat. No. 4,752,414, which is a continuation-in-part of Ser. No. 699,054, Feb. 7, 1985, abandoned.

[30] Foreign Application Priority Data

Feb. 7, 1984 [DE] Fed. Rep. of Germany ....... 3404116

[51] Int. Cl.$^4$ .................. G02F 1/13; C09K 19/34; C07D 239/02
[52] U.S. Cl. .................. 252/299.61; 252/299.5; 350/350 R; 544/315; 544/318; 544/335
[58] Field of Search .................. 252/299.61, 299.5; 350/350 R; 544/315, 318, 335

[56] References Cited

U.S. PATENT DOCUMENTS

| | | | |
|---|---|---|---|
| 4,211,610 | 7/1980 | Zasenke et al. | 252/299.61 |
| 4,273,929 | 6/1981 | Boller et al. | 252/299.61 |
| 4,358,393 | 11/1982 | Zasenke et al. | 252/299.61 |
| 4,462,423 | 7/1984 | Boller et al. | 252/299.61 |
| 4,510,069 | 4/1985 | Eidenschink et al. | 252/299.61 |
| 4,533,488 | 8/1985 | Fukui et al. | 252/299.61 |
| 4,564,694 | 1/1986 | Hirai et al. | 252/299.61 |
| 4,609,485 | 9/1986 | Kitano et al. | 252/299.61 |
| 4,621,901 | 11/1986 | Petrazilka et al. | 252/299.61 |
| 4,623,477 | 11/1986 | Ogawa et al. | 252/299.61 |
| 4,632,515 | 12/1986 | Gray et al. | 252/299.61 |
| 4,659,502 | 4/1987 | Fearon et al. | 252/299.61 |
| 4,704,227 | 11/1987 | Krause et al. | 252/299.61 |
| 4,713,197 | 12/1987 | Eidenschink et al. | 252/299.61 |
| 4,752,414 | 6/1988 | Eidenschink et al. | 252/299.61 |
| 4,755,323 | 7/1988 | Eidengehink et al. | 252/299.61 |
| 4,774,020 | 9/1988 | Kitane et al. | 252/299.61 |
| 4,776,973 | 10/1988 | Bofinger et al. | 252/299.61 |
| 4,808,333 | 2/1989 | Huynhuba et al. | 252/299.61 |
| 4,812,258 | 3/1989 | Krause et al. | 252/299.61 |
| 4,824,596 | 4/1989 | Kitano et al. | 252/299.61 |

FOREIGN PATENT DOCUMENTS

| | | | |
|---|---|---|---|
| 84194 | 7/1983 | European Pat. Off. | 252/299.61 |
| 149208 | 7/1985 | European Pat. Off. | 252/299.61 |
| 149238 | 7/1985 | European Pat. Off. | 252/299.61 |
| 3315295 | 10/1984 | Fed. Rep. of Germany | 252/299.61 |
| 3322982 | 1/1985 | Fed. Rep. of Germany | 252/299.61 |
| 3405914 | 8/1985 | Fed. Rep. of Germany | 252/299.61 |
| 3437935 | 4/1986 | Fed. Rep. of Germany | 252/299.61 |
| 144423 | 10/1980 | German Democratic Rep. | 252/299.61 |
| 145913 | 1/1981 | German Democratic Rep. | 252/299.61 |
| 59-98065 | 6/1984 | Japan | 252/299.61 |
| 60-51778 | 3/1985 | Japan | 252/299.61 |
| 60-78972 | 5/1985 | Japan | 252/299.61 |
| 60-109569 | 6/1985 | Japan | 252/299.61 |
| 60-193969 | 10/1985 | Japan | 252/299.61 |
| 63-22568 | 1/1988 | Japan | 252/299.61 |
| 2092169 | 8/1982 | United Kingdom | 252/299.61 |
| 8600067 | 1/1986 | World Int. Prop. O. | 252/299.61 |

Primary Examiner—Teddy S. Gron
Attorney, Agent, or Firm—Millen, White & Zelano

[57] ABSTRACT

Nitrogen-containing heterocyclic compounds of the formula I $$R^1-A^1-Z^1-A^2[Z^2-A^3]_n-R^2$$

wherein $R^1$ and $R^2$ in each case independently of one another are an alkyl group with 1–15 C atoms, it also being possible for one or two non-adjacent $CH_2$ groups to be replaced by O atoms and/or —CO— groups and/or —O—CO— groups and/or —CO—O— groups, and one of the radicals $R^1$ and $R^2$ is also H, F, Cl, Br or CN,

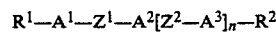 is a 1,4-cyclohexylene group, it also being possible for one or two non-adjacent $CH_2$ groups to be replaced by O atoms, a 1,4-bicyclo(2,2,2)-octylene group or a 1,3-dithiane-2,5-diyl group, $Z^1$ and $Z^2$ in each case independently of one another are —CO—O—, —O—CO—, —$CH_2CH_2$—, —$OCH_2$—, —$CH_2O$— or a single bond, $A^2$ and $A^3$ in each case independently of one another are a 1,4-phenylene group, pyrimidine-2,5-diyl group, 1,4-cyclohexylene group, it also being possible for one or two non-adjacent $CH_2$ groups to be replaced by O atoms, 1,3-dithiane-2,5-diyl group or a 1,4-bic)-cloy2,2,2)-octylene group and is 0 or 1, with the provisos that
(a) at least one of the groups $A^2$ and $A^3$ is a pyrimidine-2,5-diyl group,
(b) at least one of the groups $Z^1$ and $Z^2$ is not a single bond if $A^2$ is pyrimidine-2,5-diyl and $R^2$ is alkyl or CN,
(c) $Z^1$ is not —CO—O— if $A^3$ is pyrimidine-2,5-diyl and $A^1$ is 1,4-cyclohexylene,
(d) n is not 0 if $A^1$ is 1,4-cyclohexylene and $Z^1$ is —$CH_2CH_2$—, and
(e) $Z^1$ is not —$CH_2CH_2$— if $R^2$ is CN, and
(f) $Z^1$ is —$CH_2CH_2$—, —$OCH_2$— or —$CH_2O$—, if $A^1$ is 1,4-cyclohexylene and —$A^2$—$[Z^2-A^3]_n$—is

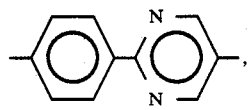

and acid addition salts thereof, can be used as components of liquid crystal phases.

6 Claims, No Drawings

NITROGEN-CONTAINING HETERCYCLIC COMPOUNDS

This is a division, of application Ser. No. 884,349, filed July 11, 1986, now U.S. Pat. No. 4,752,41 which is a continuation in part of Ser. No. 699,054, filed Feb. 7, 1985, now abandoned.

This invention relates to new compounds having valuable properties as liquid crystals.

SUMMARY OF THE INVENTION

It is an object of this invention to provide new stable liquid crystal or mesogenic compounds which are suitable as components of liquid crystal phases.

Upon further study of the specification and appended claims, further objects and advantages of this invention will become apparent to those skilled in the art.

These objects have been achieved by providing nitrogen-containing heterocyclic compounds of the formula I $$R^1-A^1-Z^1-A^2-[Z^2-A^3]_n-R^2$$

wherein $R^1$ and $R^2$ in each case independently of one another are an alkyl group with 1–15 C atoms, it also being possible for one or two non-adjacent $CH_2$ groups to be replaced by O atoms and/or —CO— groups and/or —O—CO— groups and/or —CO—O— groups, and one of the radicals $R^1$ and $R^2$ can also be H, F, Cl, Br or CN, $A^1$ is a 1,4-cyclohexylene group, it also being possible for one or two non-adjacent $CH_2$ groups to be replaced by O atoms; a 1,4-bicyclo-(2,2,2)-octylene group; or a 1,3-dithiane-2,5-diyl group, $Z^1$ and $Z^2$ in each case independently of one another are —CO—O—, —O—CO—, —CH$_2$CH$_2$—, —OCH$_2$—, —CH$_2$O— or a single bond, $A^2$ and $A^3$ in each case independently of one another are a 1,4-phenylene group; pyrimidine-2,5-diyl group, 1,4-cyclohexylene group, it also being possible for one or two non-adjacent $CH_2$ groups to be replaced by O atoms; 1,3-dithiane-2,5-diyl group; or a 1,4-bicyclo(2,2,2)-octylene group and n is 0 or 1, with the provisos that
(a) at least one of the groups $A^2$ and $A^3$ is a pyrimidine-2,5-diyl group,
(b) at least one of the groups $Z^1$ and $Z^2$ is not a single bond if $A^2$ is pyrimidine-2,5-diyl and $R^2$ is alkyl or CN,
(c) $Z^1$ is not —CO—O— if $A^3$ is pyrimidine-2,5-diyl and $A^1$ is 1,4-cyclohexylene,
(d) n is not 0 if $A^1$ is 1,4-cyclohexylene and $Z^1$ is —CH$_2$CH$_2$—,
(e) $Z^1$ is not —CH$_2$CH$_2$— if $R^2$ is CN, and
(f) $Z^1$ is —CH$_2$CH$_2$—, —OCH$_2$— or —CH$_2$O—, if $A^1$ is 1,4-cyclohexylene and —A$^2$—[Z$^2$—A$^3$]$_n$— is

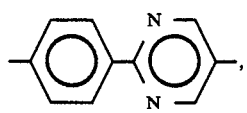

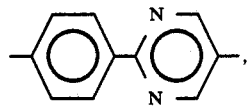

and acid addition salts thereof.

For simplicity, in the following text Cy is a 1,4-cyclohexylene group, Dio is a 1,3-dioxane-2,5-diyl group, Dit is a 1,3-dithiane-2,5-diyl group, Bi is a 1,4-bicyclo(2,2,2)-octylene group, Phe is a 1,4-phenylene group and Pyr is a pyrimidine-2,5-diyl group.

DETAILED DISCUSSION

Similar compounds are known, for example, from German patent specification No. 2,257,588. However, in contrast to the present compounds, the compounds mentioned therein contain no saturated rings (Cy, Dio, Dit or Bi).

Like similar compounds, the compounds of the formula I can be used as components of liquid crystal phases, in particular for displays which are based on the principle of the twisted cell (TN displays), the guest host effect, the effect of deformation of aligned phases or the effect of dynamic scattering.

It has been found that the compounds of the formula I are outstandingly suitable as components of liquid crystal phases. In particular, stable liquid crystal phases for TN displays with high multiplexing rates can be prepared with the aid of these compounds.

Surprisingly, when compounds of the formula I were added to liquid crystal phases, it was found that even the addition of relatively large amounts (for example 10–30%) only insignificantly increased the threshold voltage. At the same time, a considerable improvement in the steepness of the characteristic line of the mixture completely unexpectedly occurred, so that compounds of formula I are to be regarded as particularly advantageously suitable substances for the preparation of liquid crystal mixtures with a streep characteristic line.

They therefore make possible the development of mixtures of high multiplexing capacity and of very small optical anisotropy, with which a twisting cell, in particular, can be operated in the first transmission minimum according to Gooch-Tarry. A very small dependency of the contrast on the observation angle thereby results.

By providing the compounds of the formula I, the range of liquid crystal substances which are suitable, from various technological viewpoints, for the preparation of nematic mixtures is also quite generally considerably extended.

The compounds of the formula I have a wide range of applications. Depending on the choice of the substituents, these compounds can be used as base materials, from which liquid crystal dielectrics are predominantly composed; however, compounds of the formula I can also be added to liquid crystal base materials from other classes of compounds, for example in order to reduce the dielectric and/or optical anisotropy of such a dielectric. The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is advantageously located for electrooptical use. They are very stable towards chemicals, heat and light.

The invention thus relates to the compounds of the formula I and to a process for their preparation, characterized in that a compound which otherwise corresponds to the formula I but contains one or more reductible groups and/or C-C bonds instead of H atoms is treated with a reducing agent, or in that, to prepare esters of the formula I (wherein $R^1$ and/or $R^2$ are an alkyl group, in which one or two $CH_2$ groups are replaced by —O—CO— groups and/or —CO—O— groups, and/or wherein Z is —CO—O— or —O—CO—), a corresponding carboxylic acid or one of its reactive derivatives is reacted with a corresponding alcohol or one of its reactive derivatives, or in that, to prepare 1,3-dioxane derivatives or 1,3-dithiane derivatives of the formula I (wherein $A^1$ is 1,3-dioxane-2,5-diyl or 1,3-dithiane-2,5-diyl) a corresponding aldehyde is reacted with a corresponding diol or dithiol, or in that, to prepare ethers of the formula I (wherein $R^1$ and/or $R^2$ are an alkyl group, in which one or two $CH_2$ groups are replaced by O atoms, and/or Z is an —$OCH_2$— or —$CH_2O$— group), a corresponding hydroxy compound is etherified, and/or in that, if appropriate, a base of the formula I is converted into one of its acid addition salts by treatment with an acid, or in that, if appropriate, a compound of the formula I is liberated from one of its acid addition salts by treatment with a base.

The invention furthermore relates to the use of the compounds of the formula I as components of liquid crystal phases. The invention moreover relates to liquid crystal phases containing at least one compound of the formula I and to liquid crystal display elements, in particular electrooptical display elements, containing such phases.

Above and below, $R^1$, $R^2$, $A^1$, $A^2$, $A^3$, $Z^1$, $Z^2$ and n have the meaning given, unless expressly indicated otherwise.

The compounds of the formula I accordingly include compounds of the part formulae Ia and Ib (with two rings) and Ic, If, Ii and Il (with three rings):

| | |
|---|---|
| $R^1$—$A^1$—$A^2$—$R^2$ | Ia |
| $R^1$—$A^1$—$Z^1$—$A^2$—$R^2$ | Ib |
| $R^1$—$A^1$—$A^2$—$A^3$—$R^2$ | Ic |
| $R^1$—$A^1$—$Z^1$—$A^2$—$A^3$—$R^2$ | If |
| $R^1$—$A^1$—$A^2$—$Z^2$—$A^3$—$R^2$ | Ii |
| $R^1$—$A^1$—$Z^1$—$A^2$—$Z^2$—$A^3$—$R^2$ | Il |

The preferred compounds of the part formula Ia include those of the part formulae Iaa to Iad:

| | |
|---|---|
| $R^1$—Cy—Pyr—$R^2$ | Iaa |
| $R^1$—Dio—Pyr—$R^2$ | Iab |
| $R^1$—Dit—Pyr—$R^2$ | Iac |
| $R^1$—Bi—Pyr—$R^2$ | Iad |

Of these, those of the part formula Iaa are particularly preferred.

The preferred compounds of the part formula Ib include those of the part formulae Iba to Ibi:

| | |
|---|---|
| $R^1$—$A^1$—COO—Pyr—$R^2$ | Iba |
| $R^1$—$A^1$—OCO—Pyr—$R^2$ | Ibb |
| $R^1$—$A^1$—$CH_2CH_2$—Pyr—$R^2$ | Ibc |
| $R^1$—$A^1$—$CH_2O$—Pyr—$R^2$ | Ibd |
| $R^1$—$A^1$—$OCH_2$—Pyr—$R^2$ | Ibe |
| $R^1$—Cy—$Z^1$—Pyr—$R^2$ | Ibf |
| $R^1$—Dio—$Z^1$—Pyr—$R^2$ | Ibg |
| $R^1$—Dit—$Z^1$—Pyr—$R^2$ | Ibh |
| $R^1$—Bi—$Z^1$—Pyr—$R^2$ | Ibi |

Of these, those of the part formulae Ibc and Ibf are particularly preferred.

The preferred compounds of the part formula Ic include those of the part formulae Ica to Iccc:

| | |
|---|---|
| $R^1$—Cy—Pyr—Phe—$R^2$ | Ica |
| $R^1$—Cy—Phe—Pyr—$R^2$ | Icc |
| $R^1$—Cy—Pyr—Cy—$R^2$ | Ice |
| $R^1$—Cy—Cy—Pyr—$R^2$ | Icf |
| $R^1$—Cy—Pyr—Dio—$R^2$ | Icg |
| $R^1$—Dio—Pyr—Cy—$R^2$ | Ich |
| $R^1$—Cy—Dio—Pyr—$R^2$ | Ici |
| $R^1$—Dio—Cy—Pyr—$R^2$ | Icj |
| $R^1$—Cy—Pyr—Dit—$R^2$ | Ick |
| $R^1$—Dit—Pyr—Cy—$R^2$ | Icl |
| $R^1$—Cy—Dit—Pyr—$R^2$ | Icm |
| $R^1$—Dit—Cy—Pyr—$R^2$ | Icn |
| $R^1$—Cy—Pyr—Bi—$R^2$ | Ico |
| $R^1$—Bi—Pyr—Cy—$R^2$ | Icp |
| $R^1$—Cy—Bi—Pyr—$R^2$ | Icq |
| $R^1$—Bi—Cy—Pyr—$R^2$ | Icr |
| $R^1$—Dio—Pyr—Phe—$R^2$ | Ics |
| $R^1$—Dio—Phe—Pyr—$R^2$ | Icu |
| $R^1$—Dit—Pyr—Phe—$R^2$ | Icw |
| $R^1$—Dit—Phe—Pyr—$R^2$ | Icy |
| $R^1$—Bi—Pyr—Phe—$R^2$ | Icaa |
| $R^1$—Bi—Phe—Pyr—$R^2$ | Iccc |

Of these, those of the part formula Icf and compounds of the part formula Icc, wherein $R^2$ is CN, are particularly preferred.

The preferred compounds of the part formula If include those of the part formulae Ifa to Ift:

| | |
|---|---|
| $R^1-A^1-COO-A^2-A^3-R^2$ | Ifa |
| $R^1-A^1-OCO-A^2-A^3-R^2$ | Ifb |
| $R^1-A^1-CH_2CH_2-A^2-A^3-R^2$ | Ifc |
| $R^1-A^1-OCH_2-A^2-A^3-R^2$ | Ifd |
| $R^1-A^1-CH_2O-A^2-A^3-R^2$ | Ife |
| $R^1-Cy-Z^1-A^2-A^3-R^2$ | Iff |
| $R^1-Dio-Z^1-A^2-A^3-R^2$ | Ifg |
| $R^1-Dit-Z^1-A^2-A^3-R^2$ | Ifh |
| $R^1-Bi-Z^1-A^2-A^3-R^2$ | Ifi |
| $R^1-Cy-Z^1-Pyr-Phe-R^2$ | Ifj |
| $R^1-Cy-Z^1-Phe-Pyr-R^2$ | Ifk |
| $R^1-Cy-Z^1-Pyr-Cy-R^2$ | Ifl |
| $R^1-Cy-Z^1-Cy-Pyr-R^2$ | Ifm |
| $R^1-Cy-Z^1-Pyr-Dio-R^2$ | Ifn |
| $R^1-Dio-Z^1-Pyr-Phe-R^2$ | Ifo |
| $R^1-Dio-Z^1-Phe-Pyr-R^2$ | Ifp |
| $R^1-Dit-Z^1-Pyr-Phe-R^2$ | Ifq |
| $R^1-Dit-Z^1-Phe-Pyr-R^2$ | Ifr |
| $R^1-Bi-Z^1-Pyr-Phe-R^2$ | Ifs |
| $R^1-Bi-Z^1-Phe-Pyr-R^2$ | Ift |

Of these, those of the part formulae Ifc and Ife as well as Ij, and Ik and Il, are particularly preferred.

The preferred compounds of the part formula Ii include those of the part formulae Iia to Iiu:

| | |
|---|---|
| $R^1-A^1-A^2-COO-A^3-R^2$ | Iia |
| $R^1-A^1-A^2-OCO-A^3-R^2$ | Iib |
| $R^1-A^1-A^2-CH_2CH_2-A^3-R^2$ | Iic |
| $R^1-A^1-A^2-CH_2O-A^3-R^2$ | Iid |
| $R^1-A^1-A^2-OCH_2-A^3-R^2$ | Iie |
| $R^1-Cy-A^2-Z^2-A^3-R^2$ | Iif |
| $R^1-Dio-A^2-Z^2-A^3-R^2$ | Iig |
| $R^1-Dit-A^2-Z^2-A^3-R^2$ | Iih |
| $R^1-Bi-A^2-Z^2-A^3-R^2$ | Iii |
| $R^1-Cy-Pyr-Z^2-Phe-R^2$ | Iij |
| $R^1-Cy-Pyr-Z^2-Cy-R^2$ | Iik |
| $R_1-Cy-Phe-Z^2-Pyr-R^2$ | Iil |
| $R^1-Cy-Cy-Z^2-Pyr-R^2$ | Iim |
| $R^1-Dio-Cy-Z^2-Pyr-R^2$ | Iin |
| $R^1-Dit-Cy-Z^2-Pyr-R^2$ | Iio |
| $R^1-Dio-Pyr-Z^2-Phe-R^2$ | Iip |
| $R^1-Dit-Pyr-Z^2-Phe-R^2$ | Iiq |
| $R^1-Dio-Pyr-Z^2-Cy-R^2$ | Iir |
| $R^1-Dit-Pyr-Z^2-Cy-R^2$ | Iis |
| $R^1-Bi-Pyr-Z^2-Cy-R^2$ | Iit |
| $R^1-Bi-Pyr-Z^2-Phe-R^2$ | Iin |

Of these, those of the part formula Iic are particularly preferred.

The preferred compounds of the part formula II include those of the part formulae IIa to Ili:

| | |
|---|---|
| $R^1-A^1-COO-A^2-COO-A^3-R^2$ | IIa |
| $R^1-A^1-COO-A^2-OCO-A^3-R^2$ | IIb |
| $R^1-A^1-OCO-A^2-COO-A^3-R^2$ | IIc |
| $R^1-A^1-OCO-A^2-OCO-A^3-R^2$ | IId |
| $R^1-A^1-COO-A^2-CH_2CH_2-A^3-R^2$ | IIe |
| $R^1-A^1-OCO-A^2-CH_2CH_2-A^3-R^2$ | IIf |
| $R^1-A^1-CH_2CH_2-A^2-COO-A^3-R^2$ | IIg |
| $R^1-A^1-CH_2CH_2-A^2-OCO-A^3-R^2$ | IIh |
| $R^1-A^1-CH_2CH_2-A^2-CH_2CH_2-A^3-R^2$ | Ili |

Of these, those of the part formula Ili are particularly preferred.

In the compounds of the formulae above and below, $R^1$ and $R^2$ are preferable alkyl, and furthermore alkoxy, oxaalkyl or CN.

Particularly preferred are compounds of the formulae above and below, wherein $R^1$ is alkyl and $R^2$ is alkyl or alkoxy. Preferably $R^1$ and $R^2$ in each case independently of one another are straight chain alkyl groups with 1-7 C-atoms.

$A^1$ is preferably Cy or Dio, and furthermore preferably Dit or Bi. The compound of the formula I preferably contains not more than one of the radicals Dio, Dit, Pyr or Bi.

$A^2$ and $A^3$ are preferably Phe or Pyr, and furthermore preferably Cy, Dio or Dit.

$Z^1$ and $Z^2$ are preferably single bonds, and secondly preferably —CO—O—, —O—CO— or —CH$_2$CH$_2$— groups. Compounds of the formula I wherein one of the groups $Z^1$ and $Z^2$ is a single bond, —CO—O— or —O—CO—, in particular a single bond, and the other is —CH$_2$CH$_2$—, —OCH$_2$— or —CH$_2$O— are particularly preferred. —CH$_2$CH$_2$— is particularly preferred.

The alkyl radicals in the groups $R^1$ and/or $R^2$ can be straight-chain or branched. Preferably, they are straight-chain and have 2, 3, 4, 5, 6, 7, 8, 9, 10, 11 or 12 C atoms, and accordingly are preferably ethyl, propyl, butyl, pentyl, hexyl, heptyl, octyl, nonyl, decyl, undecyl or dodecyl, and furthermore methyl, tridecyl, tetradecyl or pentadecyl.

If $R^1$ and/or $R^2$ are alkyl radicals in which one ("alkoxy" or "oxaalkyl") or two ("alkoxyalkoxy" or "dioxaalkyl") CH$_2$ groups are replaced by 0 atoms, they can be straight-chain or branched. Preferably, they are straight-chain and have 2, 3, 4, 5, 6 or 7 C atoms, and are accordingly preferably ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl or 2-, 3-, 4-, 5- or 6-oxaheptyl, and furthermore methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8-or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

Compounds of the formulae I and of the part formulae above and below with branched end group substituents $R^1$ and or $R^2$ may occasionally be of importance because of a better solubility in the usual liquid crystal base materials, but in particular as chiral doping substances, if they are optionally active. Branched groups of this type as a rule contain not more than one chain branching. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propyl-pentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl and 2-octyloxy.

Of the compounds of the formulae I and of the part formulae above and below, those in which at least one of the radicals contained therein has one of the preferred meanings mentioned are preferred. Particularly preferred smaller groups of compounds are those of the formulae I1 to I22.

| | |
|---|---|
| Alkyl—Cy—Cy—Pyr—Alkyl | I1 |
| Alkyl—Cy—Cy—Pyr—Alkoxy | I2 |
| Alkyl—Dio—Cy—Pyr—Alkyl | I3 |
| Alkyl—Cy—CH2CH2—Phe—Pyr—Alkyl | I4 |
| Alkyl—Cy—CH2CH2—Phe—Pyr—Alkoxy | I5 |
| Alkyl—Cy—CH2CH2—Phe—Pyr—CN | I6 |
| Alkyl—Cy—Pyr—Phe—Alkoxy | I7 |
| Alkyl—Cy—Pyr—COO—Phe—Alkyl | I8 |
| Alkyl—Cy—Pyr—COO—Phe—Alkoxy | I9 |
| Alkyl—Cy—Pyr—COO—Phe—CN | I10 |
| Alkyl—Cy—Pyr—COO—Cy—Alkyl | I11 |
| Alkyl—CY—Pyr—Alkoxy | I12 |
| Alkyl—Cy—CH2CH2—Pyr—Phe—Alkyl | I13 |
| Alkyl—Cy—CH2CH2—Pyr—Phe—Alkoxy | I14 |
| Alkyl—Cy—CH2CH2—Pyr—Phe—CN | I15 |
| Alkyl—Cy—Pyr—CH2CH2—Phe—Alkyl | I16 |
| Alkyl—Cy—Pyr—CH2CH2—Phe—Alkoxy | I17 |
| Alkyl—Cy—Pyr—CH2CH2—Phe—CN | I18 |
| Alkyl—Cy—Pyr—CH2CH2—Cy—Alkyl | I19 |
| Alkyl—Cy—CH2—O—Phe—Pyr—Alkyl | I20 |
| Alkyl—Cy—CH2CH2—Cy—Pyr—Alkyl | I21 |
| Alkyl—Cy—Cy—CH2CH2—Pyr—Alkyl | I22 |

Of these, those of the formulae I1, I2, I4, I5, I6, I12, I13, I14, I15, I20, I21 and I22 are particularly preferred. Furthermore preferred are compounds of formula I7, wherein alkyl and alkoxy are straight chain groups with 2-12 C-Atoms.

In the above formulae I 1 to I 20, alkyl is preferably a straight-chain alkyl group with 2 to 10 C atoms and alkoxy is a straight-chain alkoxy group with 2 to 12 C atoms. Compounds of the formulae I 1 to I 20 in which a 2-oxaalkyl group with 2 to 12 C atoms is present instead of alkoxy are furthermore preferred.

Of the compounds of the formula I, those steroisomers in which the saturated rings (for example Cy, Dio and Dit) are trans-1,4-disubstituted are preferred.

Those of the abovementioned formulae which contain one or more of the groups Dio, Dit and/or Pyr in each case include the two possible 2,5-position isomers. Those of the abovementioned formulae in which a group $Z^1$ and/or $Z^2$ which is other than a single bond is linked with Pyr in the 5-position are preferred.

Particularly preferred compounds of the formula I and of the above part formulae are those wherein $R^1$ is a straight-chain alkyl group with 1 to 10 C atoms and $R^2$ is a straight-chain alkoxy, oxaalkyl or alkyl group with 2 to 15 C atoms, in particular with 5 to 12 C atoms.

Compounds of the formula I wherein $Z^1$ is —CH2CH2—, —OCH2— or —CH2O—, if $A^1$ is 1,4-cyclohexylene and —$A^2$—[$Z^2$—$A^3$]$_n$— is

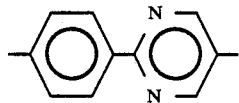

or

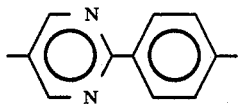

are furthermore preferred.

Preferred compounds are those of the formula I1

$$R^1-A^1-Z^1-A^2-Z^2-A^3-R^2 \qquad I1$$

wherein $R^1$ and $R^2$ in each case independently of one another are an alkyl group with 1–15 C atoms, it also being possible for one or two non-adjacent CH2 groups to be replaced by O atoms and/or —CO— groups and/or —O—CO— groups and/or —CO—O— groups, and one of the radicals $R^1$ and $R^2$ can also be H, F, Cl, Br or CN, $A^1$ is a 1,4-cyclohexylene group, it also being possible for one or two non-adjacent CH2 groups to be replaced by O atoms; a 1,4-bicyclo(2,2,2)-octylene group; or a 1,3-dithiane-2,5-diyl group, $Z^1$ and $Z^2$ in each case independently of one another are —CO—O—, —O—CO—, —CH2CH2—, —OCH2—, —CH2O— or a single bond, $A^2$ is a 1,4-phenylene group; 1,4-cyclohexylene group, it also being possible for one or two non-adjacent $CH_2$ groups to be replaced by O atoms; 1,3-dithiane-2,5-diyl group; or a 1,4-bicyclo(2,2,2)-octylene group and $A^3$ is a pyrimidine-2,5-diyl group, with the provisos that
(a) $Z^1$ is not —CO—O— if $A^3$ is pyrimidine-2,5-diyl and $A^1$ is 1,4-cyclohexylene,
(b) $Z^1$ is not —$CH_2CH_2$— if $R^2$ is CN, and (c) $Z^1$ is —$CH_2CH_2$—, —$OCH_2$— or —$CH_2O$—, if $A^1$ is 1,4-cyclohexylene and —$A^2$—[$Z^2$—$A^3$]$_n$— is

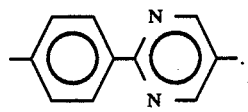

$R^1$, $R^2$, $A^1$, $A^2$, $A^3$, $Z^1$ and $Z^2$ have the preferred meanings as shown above for formula I and part formulae. Particularly preferred are compounds of formula I1, wherein one of $Z^1$ and $Z^2$ is a single bond and the other is —$CH_2CH_2$—, —$CH_2O$— or —$OCH_2$— and/or —$A^1$—$Z^1$—$A^2$— is —Cy—Cy—.

The compounds of the formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. It is also possible to utilise variants which are known per se and are not mentioned here in more detail.

The expert can find corresponding synthesis methods from the prior art by routine methods (for example German Offenlegungsschriften 2,344,732, 2,450,088, 2,429,093, 2,502,904, 2,636,684, 2,701,591 and 2,752,975 in respect of compounds with 1,4-cyclohexylene and 1,4-phenylene groups; German patent specification No. 2,641,724 in respect of compounds with pyrimidine-2,5-diyl groups; German Offenlegungsschriften 2,944,905 and 3,227,916 in respect of compounds with 1,3-dioxane-2,5-diyl groups; East German patent specification No. 160,061 in respect of compounds with 1,3-dithiane-2,5-diyl groups; U.S. Pat. No. 4,261,652 and 4,219,256 in respect of compounds with 1,4-bicyclo(2,2,2)-octylene groups; and German Offenlegungsschrift 3,201,721 in respect of compounds with —$CH_2CH_2$— bridge members.

If desired, the starting substances can also be formed in situ such that they are not isolated from the reaction mixture but are immediately reacted further to give the compounds of the formula I.

Thus, the compounds of the formula I can be prepared by reducing a compound which otherwise corresponds to the formula I but contains one or more reducible groups and/or C-C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can contain a cyclohexane ring or cyclohexanone ring instead of a cyclohexane ring, and/or a —CH=CH— group instead of a —$CH_2CH_2$— group, and/or a —CO— group instead of a —$CH_2$— group, and/or free or functionally modified (for example in the form of its p-toluene-sulfonate) OH group instead of an H atom.

The reduction can be carried out, for example, by catalytic hydrogenation at temperatures between about 0° and about 200° and under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Advantageously suitable catalysts are noble metals, such as Pt or Pd, which can be used in the form of oxides (for example $PtO_2$ or PdO), on a support (for example Pd on charcoal, calcium carbonate or strontium carbonate) or in finely divided form.

Ketones can also be reduced by the methods of Clemmensen (with zinc, zinc amalgam or tin and hydrochloric acid, advantageously in aqueous-alcoholic solution or in a heterogeneous phase system with water/toluene, at temperatures between about 80° and 120°) or Wolff-Kishner (with hydrazine, advantageously in the presence of alkali, such as KOH or NaOH, in a high boiling solvent, such as diethylene glycol or triethylene glycol, at temperatures between about 100° and 200°) to give the corresponding compounds of the formula I containing alkyl groups and/or —$CH_2CH_2$— bridges.

Reductions with complex hydrides are furthermore possible. For example, arylsulfonyloxy groups can be removed by reduction with $LiAlH_4$, and in particular p-toluenesulfonyloxymethyl groups can be reduced to methyl groups, advantageously in an inert solvent, such as diethyl ether or THF, at temperatures between about 0° and 100°. Double bonds can be hydrogenated with $NaBH_4$ or tributyl-tin hydride in methanol (even in the presence of CN groups!); thus, for example, the corresponding cyclohexane derivatives are formed from 1-cyanocyclohexane derivatives.

Esters of the formula I ($R^1$ and/or $R^2$=alkyl, in which one or two $CH_2$ groups are replaced by —O—CO— and/or —CO—O— groups, or $Z^1$ and/or $Z^2$=—CO—O— or —O—CO—) can also be obtained by esterification of corresponding carboxylic acids (or their reactive derivatives) with alcohols or phenols (or their reactive derivatives).

Particularly suitable reactive derivatives of the carboxylic acids mentioned are the acid halides, in particular the chlorides and bromides, and furthermore the anhydrides, azides or esters, in particular alkyl esters with 1-4 C atoms in the alkyl group.

Particularly suitable reactive derivatives of the alcohols or phenols mentioned are the corresponding metal alcoholates or phenolates, prferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and solfoxides, such as dimethylsulfoxide or sulfolane. Water-immiscible solvents can at the same time advantageously be used for azeotropic removal by distillation of the water formed during the esterification. An excess of an organic base, for example pyridine, quinoline or triethylamine, can occasionally also be used as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is to react an acid anhydride or, in particular, an acid chloride with an alcohol, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, with stirring, and adding a solution of the acid chloride or anhydride in diethyl ether, acetone or dimethylformamide to this suspension, advantageously at temperatures between about $-25°$ and $+20°$.

Dioxane derivatives and dithiane derivatives of the formula 1 (wherein one of the groups $A^1$ and/or $A^2$ and/or $A^3$ is a 1,3-dioxane-2,5-diyl group or a 1,3-dithiane-2,5-diyl group) are advantageously prepared by reacting a corresponding aldehyde with a corresponding 1,3-diol or a corresponding 1,3-dithiol (or one of its reactive derivatives), preferably in the presence of an inert solvent, such as benzene or toluene, and/or a catalyst, for example a strong acid, such as sulfuric acid or benzene- or p-toluene-sulfonic acid, at temperatures between about $20°$ and about $150°$, preferably between $80°$ and $120°$. Suitable reactive derivatives of the starting substances are, above all, acetals.

The aldehydes, 1,3-diols and 1,3-dithiols mentioned and their reactive derivatives are known in some cases, and some of them can be prepared without difficulty by standard processes of organic chemistry from compounds which are known from the literature. For example, the aldehydes can be obtained by oxidation of corresponding carboxylic acids or their derivatives, the diols can be obtained by reduction of corresponding diesters, and the dithiols can be obtained by reaction of corresponding dihalides with NaSH.

To prepare nitriles of the formula I (wherein $R^1$ and/or $R^2$ are CN), corresponding acid amides can be dehydrated. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ or $COCl_2$, and furthermore $P_2O_5$, $P_2S_5$, $AlCl_3$ (for example as a double compound with NaCl) and aromatic sulfonic acids and sulfonic acid halides. The dehydration can be carried out in the presence or absence of an inert solvent at temperatures between about $0°$ and $150°$; examples of possible solvents are bases, such as pyridine or triethylamine, aromatic hydrocarbons, such as benzene, toluene or xylene, or amides, such as dimethylformamide.

To prepare the abovementioned nitriles of the formula I, it is also possible to react corresponding acid halides, preferably the chlorides, with sulfamide, advantageously in an inert solvent, such as tetramethylene sulfone, at temperatures between about $80°$ and $150°$, preferably at $120°$. After customary working up, the nitriles can be isolated directly.

Ethers of the formula I (wherein $R^1$ and/or $R^2$ are an alkyl group, in which one or two $CH_2$ groups can be replaced by 0 atoms, and/or wherein $Z^1$ and/or $Z^2$ is a $-OCH_2-$ or a $-CH_2O-$ group) can be obtained by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This derivative can then be reacted with the corresponding alkyl halide or sulfonate or dialkyl sulfate, advantageously in an inert solvent, such as acetone, 1,2-dimethoxyethane, dimethylformamide or dimethylsulfoxide, or an excess of aqueous or aqueous-alcoholic NaOH or KOH, at temperatures between about $20°$ and $100°$.

A base of the formula I can be converted into the associated acid addition salt with an acid. For this reaction, it is possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono-and -di-sulfonic acids or lauryl-sulfuric acid.

Conversely, it is possible to liberate the base of the formula I from an acid addition salt of a compound of the formula I by treatment with a base, for example with a strong inorganic base, such as KOH or NaOH. Thus, the salts can be used, for example, for regeneration of the liquid crystalline compounds of formula I.

The liquid crystal phases according to the invention comprise 2 to 15, preferably 3 to 12, components, at least one of which is a compound of the formula I. The other constituents are preferably chosen from the nematic or nematogenic substances, in particular the known substances, from the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl-or cyclohexyl-pyrimidines, phenyl- or cyclohexyldioxanes, phenyl- or cyclohexyl-1,3-dithianes, 1,2-bis-cyclohexyl-ethanes, 1,2- bis-phenylethanes, 1-phenyl-2-cyclohexyl-ethanes, optionally halogenated stilbenes, benzyl phenyl ethers, tolanes and substituted cinnamic acids.

The most important compounds which are suitable as constituents of such liquid crystal phases can be characterised by the formula II

R'—L—G—E—R''     II wherein L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —CN and R' and R'' are alkyl, alkoxy, alkanoyloxy or alkoxycarbonyloxy with up to 18, preferably up to 8, carbon atoms, or one of these radicals is also CN, NC, NO$_2$, CF$_3$, F, Cl or Br.

In most of these compounds, R' and R'' are different, one of these radicals usually being an alkyl or alkoxy group. However, other variants of the envisaged substituents can also be used. Many such substances or mixtures thereof are commercially available. All of these substances can be prepared by methods which are known from the literature.

The phases according to the invention contain about 0.1 to 99%, preferably 10 to 95%, of one or more compounds of the formula I.

Dielectrics according to the invention containing 0.1 to 40%, preferably 0.5 to 30%, of one or more compounds of the formula I are furthermore preferred.

The dielectrics according to the invention are prepared in a manner which is customary per se. As a rule, the components are dissolved in one another, advantageously at elevated temperature.

The liquid crystal dielectrics according to the invention can be modified by suitable additives so that they can be used in all types of liquid crystal display elements which have hitherto been disclosed.

Such additives are known to the expert and are described in detail in the literature. For example, it is possible to add conductive salts, preferably ethyldimethyl-dodecyl-ammonium 4-hexyloxybenzoate, tetrabutyl ammonium tetraphenylboranate or complex salts of crown ethers (compare, for example, I. Haller et al., Mol. Cryst.Liq.Cryst. Volume 24, pages 249–258 (1973)) to improve the conductivity, dichroic dyestuffs to prepare colored guest/host systems, or substances for modifying the dielectric anisotropy, the viscosity and/or the orientation of the nematic phases. Such substances are described, for example, in German Offenlegungsschriften 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included with the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding test, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means: water is added, the mixture is extracted with methylene chloride, the organic phase is separated off, dried and evaporated and the product is purified by crystallization and/or chromatography.

EXAMPLE 1

65 g of trans,trans-4'-butyl-bicyclohexyl-4-carbonitrile, which is known, are dissolved in a mixture of 50 ml of ethanol and 50 ml of toluene. 27 g of HCl are passed into the solution, which is kept at 10°, in the course of 2 hours, the mixture is then stirred at room temperature for 16 hours and the resulting precipitate is filtered off with suction and washed with diethyl ether. Yield: 78 g of trans,trans-4'-butyl-bicyclohexyl-4'-carboximic acid ethyl ester hydrochloride.

77 g of the imide ester are suspended in 140 ml of ethanol and the suspension is added to a solution of 22 g of ammonia in 160 ml of ethanol at room temperature, in the course of 15 minutes. After 16 hours, the solvent is distilled off under reduced pressure. The residue is filtered off with suction and washed with diethyl ether. Yield: 67 g of trans,trans-4'-butyl-bicyclohexyl-4-carboximide-amide hydrochloride.

60 g of the carboximide-amide are heated at 150° together with 40 g of pentylmalonodialdehyde bis-diethyl acetal for 15 hours. After cooling, the residue is dissolved in ethanol. Customary working up gives 2-(trans,trans-4'-butyl-bicyclohex-4yl)-5-pentyl-pyrimidine, m.p. 67°, c.p. 158°

The following compounds are prepared analogously:
2-(trans,trans-4'-butyl-bicyclohex-4-yl)-5-ethylpyrimidine
2-(trans,trans-4'-butyl-bicyclohex-4-yl)-5-methylpyrimidine
2-(trans,trans-4'-butyl-bicyclohex-4-yl)-5-propylpyrimidine
2-(trans,trans-4'-butyl-bicyclohex-4-yl)-5-butylpyrimidine m.p. 65°, c.p. 120°
2-(trans,trans-4'-butyl-bicyclohex-4-yl)-5-hexylpyrimidine m.p. 47°, c.p. 145°

2-(trans,trans-4'-butyl-bicyclohex-4-yl)-5-heptylpyrimidine m.p. 46°; S/N 137°; c.p. 147°; Δε 3.20
2-(trans,trans-4'-ethyl-bicyclohex-4-yl)-5-ethylpyrimidine
2-(trans,trans-4'-ethyl-bicyclohex-4-yl)-5-propylpyrimidine
2-(trans,trans-4'-ethyl-bicyclohex-4-yl)-5-butylpyrimidine
2-(trans,trans-4'-ethyl-bicyclohex-4-yl)-5-pentylpyrimidine
2-(trans,trans-4'-ethyl-bicyclohex-4-yl)-5-heptylpyrimidine
2-(trans,trans-4'-ethyl-bicyclohex-4-yl)-5-methoxypyrimidine
2-(trans,trans-4'-ethyl-bicyclohex-4-yl)-5-ethoxypyrimidine
2-(trans,trans-4'-ethyl-bicyclohex-4-yl)-5-propoxypyrimidine
2-(trans,trans-4'-ethyl-bicyclohex-4-yl)-5-butoxypyrimidine
2-(trans,trans-4'-ethyl-bicyclohex-4-yl)-5-pentoxypyrimidine
2-(trans,trans-4'-ethyl-bicyclohex-4-yl)-5-heptoxypyrimidine
2-(trans,trans-4'-ethyl-bicyclohex-4-yl)-5-cyanopyrimidine
2-(trans,trans-4'-propyl-bicyclohex-4-yl)-5-ethylpyrimidine
2-(trans,trans-4'-propyl-bicyclohex-4-yl)-5-methylpyrimidine
2-(trans,trans-4'-propyl-bicyclohex-4-yl)-5-propylpyrimidine
2-(trans,trans-4'-propyl-bicyclohex-4-yl)-5-butylpyrimidine
2-(trans,trans-4'-propyl-bicyclohex-4-yl)-5-pentylpyrimidine
2-(trans,trans-4'-propyl-bicyclohex-4-yl)-5-heptylpyrimidine
2-(trans,trans-4'-propyl-bicyclohex-4-yl)-5-methoxypyrimidine
2-(trans,trans-4'-propyl-bicyclohex-4-yl)-5-ethoxypyrimidine
2-(trans,trans-4'-propyl-bicyclohex-4-yl)-5-propoxypyrimidine
2-(trans,trans-4'-propyl-bicyclohex-4-yl)-5-butoxypyrimidine
2-(trans,trans-4'-propyl-bicyclohex-4-yl)-5-pentoxypyrimidine
2-(trans,trans-4'-propyl-bicyclohex-4-yl)-5-heptoxypyrimidine
2-(trans,trans-4'-propyl-bicyclohex-4-yl)-5-cyanopyrimidine
2-(trans,trans-4'-pentyl-bicyclohex-4-yl)-5-ethylpyrimidine
2-(trans,trans-4'-pentyl-bicyclohex-4-yl)-5-methylpyrimidine
2-(trans,trans-4'-pentyl-bicyclohex-4-yl)-5-propylpyrimidine
2-(trans,trans-4'-pentyl-bicyclohex-4-yl)-5-butylpyrimidine
2-(trans,trans-4'-pentyl-bicyclohex-4-yl)-5-pentylpyrimidine
2-(trans,trans-4'-pentyl-bicyclohex-4-yl)-5-heptylpyrimidine
2-(trans,trans-4'-pentyl-bicyclohex-4-yl)-5-methoxypyrimidine
2-(trans,trans-4'-pentyl-bicyclohex-4-yl)-5-ethoxypyrimidine
2-(trans,trans-4'-pentyl-bicyclohex-4-yl)-5-propoxypyrimidine
2-(trans,trans-4'-pentyl-bicyclohex-4-yl)-5-butoxypyrimidine
2-(trans,trans-4'-pentyl-bicyclohex-4-yl)-5-pentoxypyrimidine
2-(trans,trans-4'-pentyl-bicyclohex-4-yl)-5-heptoxypyrimidine
2-(trans,trans-4'-pentyl-bicyclohex-4-yl)-5-cyanopyrimidine
2-(trans,trans-4'-heptyl-bicyclohex-4-yl)-5-ethylpyrimidine
2-(trans,trans-4'-heptyl-bicyclohex-4-yl)-5-propylpyrimidine
2-(trans,trans-4'-heptyl-bicyclohex-4-yl)-5-butylpyrimidine
2-(trans,trans-4'-heptyl-bicyclohex-4-yl)-5-pentylpyrimidine
2-(trans,trans-4'-heptyl-bicyclohex-4-yl)-5-heptylpyrimidine
2-(trans,trans-4'-heptyl-bicyclohex-4-yl)-5-methoxypyrimidine
2-(trans,trans-4'-heptyl-bicyclohex-4-yl)-5-ethoxypyrimidine
2-(trans,trans-4'-heptyl-bicyclohex-4-yl)-5-propoxypyrimidine
2-(trans,trans-4'-heptyl-bicyclohex-4-yl)-5-butoxypyrimidine
2-(trans,trans-4'-heptyl-bicyclohex-4-yl)-5-pentoxypyrimidine
2-(trans,trans-4'-heptyl-bicyclohex-4-yl)-5-heptoxypyrimidine
2-(trans,trans-4'-heptyl-bicyclohex-4-yl)-5-cyanopyrimidine
2-[trans-4-(2-trans-4-ethylcyclohexylethyl)-cyclohexyl]-5-methylpyrimidine
2-[trans-4-(2-trans-4-propylcyclohexylethyl)-cyclohexyl]-5-methylpyrimidine
2-[trans-4-(2-trans-4-butylcyclohexylethyl)-cyclohexyl]-5-methylpyrimidine
2-[trans-4-(2-trans-4-pentylcyclohexylethyl)-cyclohexyl]-5-methylpyrimidine
2-[trans-4-(2-trans-4-heptylcyclohexylethyl)-cyclohexyl]-5-methylpyrimidine
2-[trans-4-(2-trans-4-ethylcyclohexylethyl)-cyclohexyl]-5-ethylpyrimidine
2-[trans-4-(2-trans-4-propylcyclohexylethyl)-cyclohexyl]-5-ethylpyrimidine
2-[trans-4-(2-trans-4-butylcyclohexylethyl)-cyclohexyl]-5-ethylpyrimidine
2-[trans-4-(2-trans-4-pentylcyclohexylethyl)-cyclohexyl]-5-ethylpyrimidine
2-[trans-4-(2-trans-4-heptylcyclohexylethyl)-cyclohexyl]-5-ethylpyrimidine
2-[trans-4-(2-trans-4-ethylcyclohexylethyl)-cyclohexyl]-5-propylpyrimidine
2-[trans-4-(2-trans-4-propylcyclohexylethyl)-cyclohexyl]-5-propylpyrimidine
2-[trans-4-(2-trans-4-butylcyclohexylethyl)-cyclohexyl]-5-propylpyrimidine
2-[trans-4-(2-trans-4-pentylcyclohexylethyl)-cyclohexyl]-5-propylpyrimidine
2-[trans-4-(2-trans-4-heptylcyclohexylethyl)-cyclohexyl]-5-propylpyrimidine
2-[trans-4-(2-trans-4-ethylcyclohexylethyl)-cyclohexyl]-5-butylpyrimidine
2-[trans-4-(2-trans-4-propylcyclohexylethyl)-cyclohexyl]-5-butylpyrimidine 2-[trans-4-(2-trans-4-butylcyclohexylethyl)-cyclohexyl]-5-butylpyrimidine
2-[trans-4-(2-trans-4-pentylcyclohexylethyl)-cyclohexyl]-5-butylpyrimidine
2-[trans-4-(2-trans-4-heptylcyclohexylethyl)-cyclohexyl]-5-butylpyrimidine
2-[trans-4-(2-trans-4-ethylcyclohexylethyl)-cyclohexyl]-5-pentylpyrimidine
2-[trans-4-(2-trans-4-propylcyclohexylethyl)-cyclohexyl]-5-pentylpyrimidine
2-[trans-4-(2-trans-4-butylcyclohexylethyl)-cyclohexyl]-5-pentylpyrimidine
2-[trans-4-(2-trans-4-pentylcyclohexylethyl)-cyclohexyl]-5-pentylpyrimidine
2-[trans-4-(2-trans-4-heptylcyclohexylethyl)-cyclohexyl]-5-pentylpyrimidine
2-[trans-4-(2-trans-4-ethylcyclohexylethyl)-cyclohexyl]-5-heptylpyrimidine
2-[trans-4-(2-trans-4-propylcyclohexylethyl)-cyclohexyl]-5-heptylpyrimidine
2-[trans-4-(2-trans-4-butylcyclohexylethyl)-cyclohexyl]-5-heptylpyrimidine
2-[trans-4-(2-trans-4-pentylcyclohexylethyl)-cyclohexyl]-5-heptylpyrimidine
2-[trans-4-(2-trans-4-heptylcyclohexylethyl)-cyclohexyl]-5-heptylpyrimidine
2-[trans-4-(2-trans-4-ethylcyclohexylethyl)-cyclohexyl]-5-nonylpyrimidine
2-[trans-4-(2-trans-4-propylcyclohexylethyl)-cyclohexyl]-5-nonylpyrimidine
2-[trans-4-(2-trans-4-butylcyclohexylethyl)-cyclohexyl]-5-nonylpyrimidine
2-[trans-4-(2-trans-4-pentylcyclohexylethyl)-cyclohexyl]-5-nonylpyrimidine
2-[trans-4-(2-trans-4-heptylcyclohexylethyl)-cyclohexyl]-5-nonylpyrimidine
2-[trans-4-(2-trans-4-ethylcyclohexylethyl)-cyclohexyl]-5-dodecylpyrimidine
2-[trans-4-(2-trans-4-propylcyclohexylethyl)-cyclohexyl]-5-dodecylpyrimidine
2-[trans-4-(2-trans-4-butylcyclohexylethyl)-cyclohexyl]-5-dodecylpyrimidine
2-[trans-4-(2-trans-4-pentylcyclohexylethyl)-cyclohexyl]-5-dodecylpyrimidine
2-[trans-4-(2-trans-4-heptylcyclohexylethyl)-cyclohexyl]-5-dodecylpyrimidine
2-[2-trans-4-(trans-4-ethylcyclohexyl)-cyclohexylethyl]-5-methylpyrimidine
2-[2-trans-4-(trans-4-propylcyclohexyl)-cyclohexylethyl]-5-methylpyrimidine
2-[2-trans-4-(trans-4-butylcyclohexyl)-cyclohexylethyl]-5-methylpyrimidine
2-[2-trans-4-(trans-4-pentylcyclohexyl)-cyclohexylethyl]-5-methylpyrimidine
2-[2-trans-4-(trans-4-heptylcyclohexyl)-cyclohexylethyl]-5-methylpyrimidine
2-[2-trans-4-(trans-4-ethylcyclohexyl)-cyclohexylethyl]-5-ethylpyrimidine
2-[2-trans-4-(trans-4-propylcyclohexyl)-cyclohexylethyl]-5-ethylpyrimidine
2-[2-trans-4-(trans-4-butylcyclohexyl)-cyclohexylethyl]-5-ethylpyrimidine
2-[2-trans-4-(trans-4-pentylcyclohexyl)-cyclohexylethyl]-5-ethylpyrimidine
2-[2-trans-4-(trans-4-heptylcyclohexyl)-cyclohexylethyl]-5-ethylpyrimidine
2-[2-trans-4-(trans-4-ethylcyclohexyl)-cyclohexylethyl]-5-propylpyrimidine
2-[2-trans-4-(trans-4-propylcyclohexyl)-cyclohexylethyl]-5-propylpyrimidine
2-[2-trans-4-(trans-4-butylcyclohexyl)-cyclohexylethyl]-5-propylpyrimidine
2-[2-trans-4-(trans-4-pentylcyclohexyl)-cyclohexylethyl]-5-propylpyrimidine
2-[2-trans-4-(trans-4-heptylcyclohexyl)-cyclohexylethyl]-5-propylpyrimidine
2-[2-trans-4-(trans-4-ethylcyclohexyl)-cyclohexylethyl]-5-butylpyrimidine
2-[2-trans-4-(trans-4-propylcyclohexyl)-cyclohexylethyl]-5-butylpyrimidine
2-[2-trans-4-(trans-4-butylcyclohexyl)-cyclohexylethyl]-5-butylpyrimidine
2-[2-trans-4-(trans-4-pentylcyclohexyl)-cyclohexylethyl]-5-butylpyrimidine
2-[2-trans-4-(trans-4-heptylcyclohexyl)-cyclohexylethyl]-5-butylpyrimidine
2-[2-trans-4-(trans-4-ethylcyclohexyl)-cyclohexylethyl]-5-pentylpyrimidine
2-[2-trans-4-(trans-4-propylcyclohexyl)-cyclohexylethyl]-5-pentylpyrimidine
2-[2-trans-4-(trans-4-butylcyclohexyl)-cyclohexylethyl]-5-pentylpyrimidine
2-[2-trans-4-(trans-4-pentylcyclohexyl)-cyclohexylethyl]-5-pentylpyrimidine
2-[2-trans-4-(trans-4-heptylcyclohexyl)-cyclohexylethyl]-5-pentylpyrimidine
2-[2-trans-4-(trans-4-ethylcyclohexyl)-cyclohexylethyl]-5-heptylpyrimidine
2-[2-trans-4-(trans-4-propylcyclohexyl)-cyclohexylethyl]-5-heptylpyrimidine
2-[2-trans-4-(trans-4-butylcyclohexyl)-cyclohexylethyl]-5-heptylpyrimidine
2-[2-trans-4-(trans-4-pentylcyclohexyl)-cyclohexylethyl]-5-heptylpyrimidine
2-[2-trans-4-(trans-4-heptylcyclohexyl)-cyclohexylethyl]-5-heptylpyrimidine
2-[2-trans-4-(trans-4-ethylcyclohexyl)-cyclohexylethyl]-5-nonylpyrimidine
2-[2-trans-4-(trans-4-propylcyclohexyl)-cyclohexylethyl]-5-nonylpyrimidine
2-[2-trans-4-(trans-4-butylcyclohexyl)-cyclohexylethyl]-5-nonylpyrimidine
2-[2-trans-4-(trans-4-pentylcyclohexyl)-cyclohexylethyl]-5-nonylpyrimidine
2-[2-trans-4-(trans-4-heptylcyclohexyl)-cyclohexylethyl]-5-nonylpyrimidine
2-[2-trans-4-(trans-4-ethylcyclohexyl)-cyclohexylethyl]-5-dodecylpyrimidine
2-[2-trans-4-(trans-4-propylcyclohexyl)-cyclohexylethyl]-5-dodecylpyrimidine
2-[2-trans-4-(trans-4-butylcyclohexyl)-cyclohexylethyl]-5-dodecylpyrimidine
2-[2-trans-4-(trans-4-pentylcyclohexyl)-cyclohexylethyl]-5-dodecylpyrimidine
2-[2-trans-4-(trans-4-heptylcyclohexyl)-cyclohexylethyl]-5-dodecylpyrimidine
2-(2-trans-4-ethylcyclohexylethyl)-5-p-methoxyphenylpyrimidine
2-(2-trans-4-propylcyclohexylethyl)-5-p-methoxyphenylpyrimidine
2-(2-trans-4-butylcyclohexylethyl)-5-p-methoxyphenylpyrimidine
2-(2-trans-4-pentylcyclohexylethyl)-5-p-methoxyphenylpyrimidine
2-(2-trans-4-heptylcyclohexylethyl)-5-p-methoxyphenylpyrimidine 2-(2-trans-4-ethylcyclohexylethyl)-5-p-ethoxyphenyl-pyrimidine
2-(2-trans-4-propylcyclohexylethyl)-5-p-ethoxyphenyl-pyrimidine
2-(2-trans-4-butylcyclohexylethyl)-5-p-ethoxyphenyl-pyrimidine
2-(2-trans-4-pentylcyclohexylethyl)-5-p-ethoxyphenyl-pyrimidine
2-(2-trans-4-heptylcyclohexylethyl)-5-p-ethoxyphenyl-pyrimidine
2-(2-trans-4-ethylcyclohexylethyl)-5-p-propoxyphenyl-pyrimidine
2-(2-trans-4-propylcyclohexylethyl)-5-p-propoxy-phenylpyrimidine
2-(2-trans-4-butylcyclohexylethyl)-5-p-propoxyphenyl-pyrimidine
2-(2-trans-4-pentylcyclohexylethyl)-5-p-propoxy-phenylpyrimidine
2-(2-trans-4-heptylcyclohexylethyl)-5-p-propoxy-phenylpyrimidine
2-(2-trans-4-ethylcyclohexylethyl)-5-p-butoxyphenyl-pyrimidine
2-(2-trans-4-propylcyclohexylethyl)-5-p-butoxyphenyl-pyrimidine
2-(2-trans-4-butylcyclohexylethyl)-5-p-butoxyphenyl-pyrimidine
2-(2-trans-4-pentylcyclohexylethyl)-5-p-butoxyphenyl-pyrimidine
2-(2-trans-4-heptylcyclohexylethyl)-5-p-butoxyphenyl-pyrimidine
2-(2-trans-4-ethylcyclohexylethyl)-5-p-heptoxyphenyl-pyrimidine
2-(2-trans-4-propylcyclohexylethyl)-5-p-heptoxy-phenylpyrimidine
2-(2-trans-4-butylcyclohexylethyl)-5-p-heptoxyphenyl-pyrimidine
2-(2-trans-4-pentylcyclohexylethyl)-5-p-heptoxy-phenylpyrimidine
2-(2-trans-4-heptylcyclohexylethyl)-5-p-heptoxy-phenylpyrimidine
2-(2-trans-4-ethylcyclohexylethyl)-5-p-nonoxyphenyl-pyrimidine
2-(2-trans-4-propylcyclohexylethyl)-5-p-nonoxyphenyl-pyrimidine
2-(2-trans-4-butylcyclohexylethyl)-5-p-nonoxyphenyl-pyrimidine
2-(2-trans-4-pentylcyclohexylethyl)-5-p-nonoxyphenyl-pyrimidine
2-(2-trans-4-heptylcyclohexylethyl)-5-p-nonoxyphenyl-pyrimidine
2-(2-trans-4-ethylcyclohexylethyl)-5-p-methylphenyl-pyrimidine
2-(2-trans-4-propylcyclohexylethyl)-5-p-methylphenyl-pyrimidine
2-(2-trans-4-butylcyclohexylethyl)-5-p-methylphenyl-pyrimidine
2-(2-trans-4-pentylcyclohexylethyl)-5-p-methylphenyl-pyrimidine
2-(2-trans-4-heptylcyclohexylethyl)-5-p-methylphenyl-pyrimidine
2-(2-trans-4-ethylcyclohexylethyl)-5-p-propylphenyl-pyrimidine
2-(2-trans-4-propylcyclohexylethyl)-5-p-propylphenyl-pyrimidine
2-(2-trans-4-butylcyclohexylethyl)-5-p-propylphenyl-pyrimidine
2-(2-trans-4-pentylcyclohexylethyl)-5-p-propylphenyl-pyrimidine
2-(2-trans-4-heptylcyclohexylethyl)-5-p-propylphenyl-pyrimidine
2-(2-trans-4-ethylcyclohexylethyl)-5-p-butylphenyl-pyrimidine
2-(2-trans-4-propylcyclohexylethyl)-5-p-butylphenyl-pyrimidine
2-(2-trans-4-butylcyclohexylethyl)-5-p-butylphenyl-pyrimidine
2-(2-trans-4-pentylcyclohexylethyl)-5-p-butylphenyl-pyrimidine, m.p. 85°, c.p. 121°
2-(2-trans-4-heptylcyclohexylethyl)-5-p-butylphenyl-pyrimidine
2-(2-trans-4-ethylcyclohexylethyl)-5-p-pentylphenyl-pyrimidine
2-(2-trans-4-propylcyclohexylethyl)-5-p-pentylphenyl-pyrimidine
2-(2-trans-4-butylcyclohexylethyl)-5-p-pentylphenyl-pyrimidine
2-(2-trans-4-pentylcyclohexylethyl)-5-p-pentylphenyl-pyrimidine
2-(2-trans-4-heptylcyclohexylethyl)-5-p-pentylphenyl-pyrimidine
2-(2-p-methylphenylethyl)-5-(trans-4-ethylcyclohexyl)-pyrimidine
2-(2-p-ethylphenylethyl)-5-(trans-4-ethylcyclohexyl)-pyrimidine
2-(2-p-propylphenylethyl)-5-(trans-4-ethylcyclohexyl)-pyrimidine
2-(2-p-butylphenylethyl)-5-(trans-4-ethylcyclohexyl)-pyrimidine
2-(2-p-pentylphenylethyl)-5-(trans-4-ethylcyclohexyl)-pyrimidine
2-(2-p-methylphenylethyl)-5-(trans-4-propylcyclohexyl)-pyrimidine
2-(2-p-ethylphenylethyl)-5-(trans-4-propylcyclohexyl)-pyrimidine
2-(2-p-propylphenylethyl)-5-(trans-4-propylcyclohexyl)-pyrimidine
2-(2-p-butylphenylethyl)-5-(trans-4-propylcyclohexyl)-pyrimidine
2-(2-p-pentylphenylethyl)-5-(trans-4-propylcyclohexyl)-pyrimidine
2-(2-p-methylphenylethyl)-5-(trans-4-pentylcyclohexyl)-pyrimidine
2-(2-p-ethylphenylethyl)-5-(trans-4-pentylcyclohexyl)-pyrimidine
2-(2-p-propylphenylethyl)-5-(trans-4-pentylcyclohexyl)-pyrimidine
2-(2-p-butylphenylethyl)-5-(trans-4-pentylcyclohexyl)-pyrimidine, m.p. 51°, c.p. 141°
2-(2-p-pentylphenylethyl)-5-(trans-4-pentylcyclohexyl)-pyrimidine
2-(2-trans-4-ethylcyclohexylethyl)-5-(trans-4-ethylcyclohexyl)-pyrimidine
2-(2-trans-4-propylcyclohexylethyl)-5-(trans-4-ethylcyclohexyl)-pyrimidine
2-(2-trans-4-butylcyclohexylethyl)-5-(trans-4-ethylcyclohexyl)-pyrimidine
2-(2-trans-4-pentylcyclohexylethyl)-5-(trans-4-ethylcyclohexyl)-pyrimidine
2-(2-trans-4-heptylcyclohexylethyl)-5-(trans-4-ethylcyclohexyl)-pyrimidine
2-(2-trans-4-ethylcyclohexylethyl)-5-(trans-4-propylcyclohexyl)-pyrimidine
2-(2-trans-4-propylcyclohexylethyl)-5-(trans-4-propylcyclohexyl)-pyrimidine
2-(2-trans-4-butylcyclohexylethyl)-5-(trans-4-propylcyclohexyl)-pyrimidine 2-(2-trans-4-pentylcyclohexylethyl)-5-(trans-4-propyl-cyclohexyl)-pyrimidine
2-(2-trans-4-heptylcyclohexylethyl)-5-(trans-4-propyl-cyclohexyl)-pyrimidine
2-(2-trans-4-ethylcyclohexylethyl)-5-(trans-4-pentylcyclohexyl)-pyrimidine
2-(2-trans-4-propylcyclohexylethyl)-5-(trans-4-pentylcyclohexyl)-pyrimidine, m.p. 82°, b.p. 151°
2-(2-trans-4-butylcyclohexylethyl)-5-(trans-4-pentylcyclohexyl)-pyrimidine
2-(2-trans-4-pentylcyclohexylethyl)-5-(trans-4-pentylcyclohexyl)-pyrimidine
2-(2-trans-4-heptylcyclohexylethyl)-5-(trans-4-pentylcyclohexyl)-pyrimidine.

EXAMPLE 2

2-[4-(2-trans-4-Propylcyclohexylethyl)-phenyl]-5-pentyl-pyrimidine is prepared analogously to Example 1 from 4-(2-trans-4-propylcyclohexyl-ethyl)-benzonitrile, which is known, via the corresponding carboxylic acid ethyl ester hydrochloride and the carboximide-amide hydrochloride.

The following compounds are prepared analogously:
2-[4-(2-trans-4-propylcyclohexylethyl)-phenyl]-5-ethyl-pyrimidine
2-[4-(2-trans-4-propylcyclohexylethyl)-phenyl]-5-propylpyrimidine
2-[4-(2-trans-4-propylcyclohexylethyl)-phenyl]-5-butyl-pyrimidine
2-[4-(2-trans-4-propylcyclohexylethyl)-phenyl]-5-heptylpyrimidine, m.p. 99°; c.p. 138°; Δε 1.90
2-[4-(2-trans-4-propylcyclohexylethyl)-phenyl]-5-ethoxypyrimidine
2-[4-(2-trans-4-propylcyclohexylethyl)-phenyl]-5-propoxypyrimidine
2-[4-(2-trans-4-propylcyclohexylethyl)-phenyl]-5-pentyloxypyrimidine
2-[4-(2-trans-4-propylcyclohexylethyl)-phenyl]-5-nonyloxypyrimidine
2-[4-(2-trans-4-propylcyclohexylethyl)-phenyl]-5-cyanopyrimidine
2-[4-(2-trans-4-ethylcyclohexylethyl)-phenyl]-5-ethyl-pyrimidine
2-[4-(2-trans-4-ethylcyclohexylethyl)-phenyl]-5-propyl-pyrimidine
2-[4-(2-trans-4-ethylcyclohexylethyl)-phenyl]-5-butyl-pyrimidine
2-[4-(2-trans-4-ethylcyclohexylethyl)-phenyl]-5-pentyl-pyrimidine
2-[4-(2-trans-4-ethylcyclohexylethyl)-phenyl]-5-heptyl-pyrimidine
2-[4-(2-trans-4-ethylcyclohexylethyl)-phenyl]-5-nonyl-pyrimidine
2-[4-(2-trans-4-ethylcyclohexylethyl)-phenyl]-5-ethoxypyrimidine
2-[4-(2-trans-4-ethylcyclohexylethyl)-phenyl]-5-methoxypyrimidine
2-[4-(2-trans-4-ethylcyclohexylethyl)-phenyl]-5-propoxypyrimidine
2-[4-(2-trans-4-ethylcyclohexylethyl)-phenyl]-5-butoxypyrimidine
2-[4-(2-trans-4-ethylcyclohexylethyl)-phenyl]-5-pentoxypyrimidine
2-[4-(2-trans-4-ethylcyclohexylethyl)-phenyl]-5-hexoxypyrimidine
2-[4-(2-trans-4-ethylcyclohexylethyl)-phenyl]-5-nonoxypyrimidine
2-[4-(2-trans-4-ethylcyclohexylethyl)-phenyl]-5-cyanopyrimidine
2-[4-(2-trans-4-butylcyclohexylethyl)-phenyl]-5-ethylpyrimidine
2-[4-(2-trans-4-butylcyclohexylethyl)-phenyl]-5-propylpyrimidine
2-[4-(2-trans-4-butylcyclohexylethyl)-phenyl]-5-butylpyrimidine
2-[4-(2-trans-4-butylcyclohexylethyl)-phenyl]-5-pentylpyrimidine
2-[4-(2-trans-4-butylcyclohexylethyl)-phenyl]-5-heptylpyrimidine
2-[4-(2-trans-4-butylcyclohexylethyl)-phenyl]-5-nonylpyrimidine
2-[4-(2-trans-4-butylcyclohexylethyl)-phenyl]-5-ethoxypyrimidine
2-[4-(2-trans-4-butylcyclohexylethyl)-phenyl]-5-methoxypyrimidine
2-[4-(2-trans-4-butylcyclohexylethyl)-phenyl]-5-propoxypyrimidine
2-[4-(2-trans-4-butylcyclohexylethyl)-phenyl]-5-butoxypyrimidine
2-[4-(2-trans-4-butylcyclohexylethyl)-phenyl]-5-pentoxypyrimidine
2-[4-(2-trans-4-butylcyclohexylethyl)-phenyl]-5-hexoxypyrimidine
2-[4-(2-trans-4-butylcyclohexylethyl)-phenyl]-5-nonoxypyrimidine
2-[4-(2-trans-4-butylcyclohexylethyl)-phenyl]-5-cyanopyrimidine
2-[4-(2-trans-4-pentylcyclohexylethyl)-phenyl]-5-ethylpyrimidine
2-[4-(2-trans-4-pentylcyclohexylethyl)-phenyl]-5-propylpyrimidine
2-[4-(2-trans-4-pentylcyclohexylethyl)-phenyl]-5-butylpyrimidine
2-[4-(2-trans-4-pentylcyclohexylethyl)-phenyl]-5-pentyl-pyrimidine
2-[4-(2-trans-4-pentylcyclohexylethyl)-phenyl]-5-heptyl-pyrimidine
2-[4-(2-trans-4-pentylcyclohexylethyl)-phenyl]-5-nonyl-pyrimidine
2-[4-(2-trans-4-pentylcyclohexylethyl)-phenyl]-5-ethoxypyrimidine
2-[4-(2-trans-4-pentylcyclohexylethyl)-phenyl]-5-methoxypyrimidine
2-[4-(2-trans-4-pentylcyclohexylethyl)-phenyl]-5-propoxypyrimidine
2-[4-(2-trans-4-pentylcyclohexylethyl)-phenyl]-5-butoxypyrimidine
2-[4-(2-trans-4-pentylcyclohexylethyl)-phenyl]-5-pentoxypyrimidine
2-[4-(2-trans-4-pentylcyclohexylethyl)-phenyl]-5-hexoxypyrimidine
2-[4-(2-trans-4-pentylcyclohexylethyl)-phenyl]-5-nonoxypyrimidine
2-[4-(2-trans-4-pentylcyclohexylethyl)-phenyl]-5-cyanopyrimidine
2-[4-(2-trans-4-heptylcyclohexylethyl)-phenyl]-5-ethylpyrimidine
2-[4-(2-trans-4-heptylcyclohexylethyl)-phenyl]-5-propylpyrimidine
2-[4-(2-trans-4-heptylcyclohexylethyl)-phenyl]-5-butylpyrimidine
2-[4-(2-trans-4-heptylcyclohexylethyl)-phenyl]-5-pentylpyrimidine
2-[4-(2-trans-4-heptylcyclohexylethyl)-phenyl]-5-heptylpyrimidine 2-[4-(2-trans-4-heptylcyclohexylethyl)-phenyl]-5-nonyl-pyrimidine
2-[4-(2-trans-4-heptylcyclohexylethyl)-phenyl]-5-ethoxypyrimidine
2-[4-(2-trans-4-heptylcyclohexylethyl)-phenyl]-5-methoxypyrimidine
2-[4-(2-trans-4-heptylcyclohexylethyl)-phenyl]-5-propoxypyrimidine
2-[4-(2-trans-4-heptylcyclohexylethyl)-phenyl]-5-butoxypyrimidine
2-[4-(2-trans-4-heptylcyclohexylethyl)-phenyl]-5-pentoxypyrimidine
2-[4-(2-trans-4-heptylcyclohexylethyl)-phenyl]-5-hexoxypyrimidine
2-[4-(2-trans-4-heptylcyclohexylethyl)-phenyl]-5-nonoxypyrimidine
2-[4-(2-trans-4-heptylcyclohexylethyl)-phenyl]-5-cyanopyrimidine
2-p-cyanophenyl-5-[2-(trans-4-ethylcyclohexyl)-ethyl]-pyrimidine
2-p-cyanophenyl-5-[2-(trans-4-propylcyclohexyl)-ethyl]-pyrimidine
2-p-cyanophenyl-5-[2-(trans-4-butylcyclohexyl)-ethyl]-pyrimidine
2-p-cyanophenyl-5-[2-(trans-4-pentylcyclohexyl)-ethyl]-pyrimidine
2-p-cyanophenyl-5-[2-(trans-4-heptylcyclohexyl)-ethyl]-pyrimidine
2-p-cyanophenyl-5-[2-(trans-4-nonylcyclohexyl)-ethyl]-pyrimidine
2-p-fluorophenyl-5-[2-(trans-4-ethylcyclohexyl)-ethyl]-pyrimidine
2-p-fluorophenyl-5-[2-(trans-4-propylcyclohexyl)-ethyl]-pyrimidine
2-p-fluorophenyl-5-[2-(trans-4-butylcyclohexyl)-ethyl]-pyrimidine
2-p-fluorophenyl-5-[2-(trans-4-pentylcyclohexyl)-ethyl]-pyrimidine
2-p-fluorophenyl-5-[2-(trans-4-heptylcyclohexyl)-ethyl]-pyrimidine
2-p-fluorophenyl-5-[2-(trans-4-nonylcyclohexyl)-ethyl]-pyrimidine
2-p-ethylphenyl-5-[2-(trans-4-ethylcyclohexyl)-ethyl]-pyrimidine
2-p-ethylphenyl-5-[2-(trans-4-propylcyclohexyl)-ethyl]-pyrimidine
2-p-ethylphenyl-5-[2-(trans-4-butylcyclohexyl)-ethyl]-pyrimidine
2-p-ethylphenyl-5-[2-(trans-4-pentylcyclohexyl)-ethyl]-pyrimidine
2-p-ethylphenyl-5-[2-(trans-4-heptylcyclohexyl)-ethyl]-pyrimidine
2-p-ethylphenyl-5-[2-(trans-4-nonylcyclohexyl)-ethyl]-pyrimidine
2-p-butylphenyl-5-[2-(trans-4-ethylcyclohexyl)-ethyl]-pyrimidine
2-p-butylphenyl-5-[2-(trans-4-propylcyclohexyl)-ethyl]-pyrimidine
2-p-butylphenyl-5-[2-(trans-4-butylcyclohexyl)-ethyl]-pyrimidine
2-p-butylphenyl-5-[2-(trans-4-pentylcyclohexyl)-ethyl]-pyrimidine
2-p-butylphenyl-5-[2-(trans-4-heptylcyclohexyl)-ethyl]-pyrimidine
2-p-butylphenyl-5-[2-(trans-4-nonylcyclohexyl)-ethyl]-pyrimidine
2-p-pentylphenyl-5-[2-(trans-4-ethylcyclohexyl)-ethyl]-pyrimidine
2-p-pentylphenyl-5-[2-(trans-4-propylcyclohexyl)-ethyl]-pyrimidine
2-p-pentylphenyl-5-[2-(trans-4-butylcyclohexyl)-ethyl]-pyrimidine
2-p-pentylphenyl-5-[2-(trans-4-pentylcyclohexyl)-ethyl]-pyrimidine
2-p-pentylphenyl-5-[2-(trans-4-heptylcyclohexyl)-ethyl]-pyrimidine
2-p-pentylphenyl-5-[2-(trans-4-nonylcyclohexyl)-ethyl]-pyrimidine
2-p-heptylphenyl-5-[2-(trans-4-ethylcyclohexyl)-ethyl]-pyrimidine
2-p-heptylphenyl-5-[2-(trans-4-propylcyclohexyl)-ethyl]-pyrimidine
2-p-heptylphenyl-5-[2-(trans-4-butylcyclohexyl)-ethyl]-pyrimidine
2-p-heptylphenyl-5-[2-(trans-4-pentylcyclohexyl)-ethyl]-pyrimidine
2-p-heptylphenyl-5-[2-(trans-4-heptylcyclohexyl)-ethyl]-pyrimidine
2-p-heptylphenyl-5-[2-(trans-4-nonylcyclohexyl)-ethyl]-pyrimidine
2-p-hexylphenyl-5-[2-(trans-4-ethylcyclohexyl)-ethyl]-pyrimidine
2-p-hexylphenyl-5-[2-(trans-4-propylcyclohexyl)-ethyl]-pyrimidine
2-p-hexylphenyl-5-[2-(trans-4-butylcyclohexyl)-ethyl]-pyrimidine
2-p-hexylphenyl-5-[2-(trans-4-pentylcyclohexyl)-ethyl]-pyrimidine
2-p-hexylphenyl-5-[2-(trans-4-heptylcyclohexyl)-ethyl]-pyrimidine
2-p-hexylphenyl-5-[2-(trans-4-nonylcyclohexyl)-ethyl]-pyrimidine
2-p-nonylphenyl-5-[2-(trans-4-ethylcyclohexyl)-ethyl]-pyrimidine
2-p-nonylphenyl-5-[2-(trans-4-propylcyclohexyl)-ethyl]-pyrimidine
2-p-nonylphenyl-5-[2-(trans-4-butylcyclohexyl)-ethyl]-pyrimidine
2-p-nonylphenyl-5-[2-(trans-4-pentylcyclohexyl)-ethyl]-pyrimidine
2-p-nonylphenyl-5-[2-(trans-4-heptylcyclohexyl)-ethyl]-pyrimidine
2-p-nonylphenyl-5-[2-(trans-4-nonylcyclohexyl)-ethyl]-pyrimidine
2-p-methoxyphenyl-5-[2-(trans-4-ethylcyclohexyl)-ethyl]-pyrimidine
2-p-methoxyphenyl-5-[2-(trans-4-propylcyclohexyl)-ethyl]-pyrimidine
2-p-methoxyphenyl-5-[2-(trans-4-butylcyclohexyl)-ethyl]-pyrimidine
2-p-methoxyphenyl-5-[2-(trans-4-pentylcyclohexyl)-ethyl]-pyrimidine
2-p-methoxyphenyl-5-[2-(trans-4-heptylcyclohexyl)-ethyl]-pyrimidine
2-p-methoxyphenyl-5-[2-(trans-4-nonylcyclohexyl)-ethyl]-pyrimidine
2-p-pentoxyphenyl-5-[2-(trans-4-ethylcyclohexyl)-ethyl]-pyrimidine
2-p-pentoxyphenyl-5-[2-(trans-4-propylcyclohexyl)-ethyl]-pyrimidine
2-p-pentoxyphenyl-5-[2-(trans-4-butylcyclohexyl)-ethyl]-pyrimidine
2-p-pentoxyphenyl-5-[2-(trans-4-pentylcyclohexyl)-ethyl]-pyrimidine
2-p-pentoxyphenyl-5-[2-(trans-4-heptylcyclohexyl)-ethyl]-pyrimidine 2-p-pentoxyphenyl-5-[2-(trans-4-nonylcyclohexyl)-ethyl]-pyrimidine
2-p-hexoxyphenyl-5-[2-(trans-4-ethylcyclohexyl)-ethyl]-pyrimidine
2-p-hexoxyphenyl-5-[2-(trans-4-propylcyclohexyl)-ethyl]-pyrimidine
2-p-hexoxyphenyl-5-[2-(trans-4-butylcyclohexyl)-ethyl]-pyrimidine
2-p-hexoxyphenyl-5-[2-(trans-4-pentylcyclohexyl)-ethyl]-pyrimidine
2-p-hexoxyphenyl-5-[2-(trans-4-heptylcyclohexyl)-ethyl]-pyrimidine
2-p-hexoxyphenyl-5-[2-(trans-4-nonylcyclohexyl)-ethyl]-pyrimidine
2-p-heptoxyphenyl-5-[2-(trans-4-ethylcyclohexyl)-ethyl]-pyrimidine
2-p-heptoxyphenyl-5-[2-(trans-4-propylcyclohexyl)-ethyl]-pyrimidine
2-p-heptoxyphenyl-5-[2-(trans-4-butylcyclohexyl)-ethyl]-pyrimidine
2-p-heptoxyphenyl-5-[2-(trans-4-pentylcyclohexyl)-ethyl]-pyrimidine
2-p-heptoxyphenyl-5-[2-(trans-4-heptylcyclohexyl)-ethyl]-pyrimidine
2-p-heptoxyphenyl-5-[2-(trans-4-nonylcyclohexyl)-ethyl]-pyrimidine
2-p-octoxyphenyl-5-[2-(trans-4-ethylcyclohexyl)-ethyl]-pyrimidine
2-p-octoxyphenyl-5-[2-(trans-4-propylcyclohexyl)-ethyl]-pyrimidine
2-p-octoxyphenyl-5-[2-(trans-4-butylcyclohexyl)-ethyl]-pyrimidine
2-p-octoxyphenyl-5-[2-(trans-4-pentylcyclohexyl)-ethyl]-pyrimidine
2-p-octoxyphenyl-5-[2-(trans-4-heptylcyclohexyl)-ethyl]-pyrimidine
2-p-octoxyphenyl-5-[2-(trans-4-nonylcyclohexyl)-ethyl]-pyrimidine
2-p-nonoxyphenyl-5-[2-(trans-4-ethylcyclohexyl)-ethyl]-pyrimidine
2-p-nonoxyphenyl-5-[2-(trans-4-propylcyclohexyl)-ethyl]-pyrimidine
2-p-nonoxyphenyl-5-[2-(trans-4-butylcyclohexyl)-ethyl]-pyrimidine
2-p-nonoxyphenyl-5-[2-(trans-4-pentylcyclohexyl)-ethyl]-pyrimidine
2-p-nonoxyphenyl-5-[2-(trans-4-heptylcyclohexyl)-ethyl]-pyrimidine
2-p-nonoxyphenyl-5-[2-(trans-4-nonylcyclohexyl)-ethyl]-pyrimidine
2-p-decoxyphenyl-5-[2-(trans-4-ethylcyclohexyl)-ethyl]-pyrimidine
2-p-decoxyphenyl-5-[2-(trans-4-propylcyclohexyl)-ethyl]-pyrimidine
2-p-decoxyphenyl-5-[2-(trans-4-butylcyclohexyl)-ethyl]-pyrimidine
2-p-decoxyphenyl-5-[2-(trans-4-pentylcyclohexyl)-ethyl]-pyrimidine
2-p-decoxyphenyl-5-[2-(trans-4-heptylcyclohexyl)-ethyl]-pyrimidine
2-p-decoxyphenyl-5-[2-(trans-4-nonylcyclohexyl)-ethyl]-pyrimidine
2-p-undecoxyphenyl-5-[2-(trans-4-ethylcyclohexyl)-ethyl]-pyrimidine
2-p-undecoxyphenyl-5-[2-(trans-4-propylcyclohexyl)-ethyl]-pyrimidine
2-p-undecoxyphenyl-5-[2-(trans-4-butylcyclohexyl)-ethyl]-pyrimidine
2-p-undecoxyphenyl-5-[2-(trans-4-pentylcyclohexyl)-ethyl]-pyrimidine
2-p-undecoxyphenyl-5-[2-(trans-4-heptylcyclohexyl)-ethyl]-pyrimidine
2-p-undecoxyphenyl-5-[2-(trans-4-nonylcyclohexyl)-ethyl]-pyrimidine
2-p-dodecoxyphenyl-5-[2-(trans-4-ethylcyclohexyl)-ethyl]-pyrimidine
2-p-dodecoxyphenyl-5-[2-(trans-4-propylcyclohexyl)-ethyl]-pyrimidine
2-p-dodecoxyphenyl-5-[2-(trans-4-butylcyclohexyl)-ethyl]-pyrimidine
2-p-dodecoxyphenyl-5-[2-(trans-4-pentylcyclohexyl)-ethyl]-pyrimidine
2-p-dodecoxyphenyl-5-[2-(trans-4-heptylcyclohexyl)-ethyl]-pyrimidine
2-p-dodecoxyphenyl-5-[2-(trans-4-nonylcyclohexyl)-ethyl]-pyrimidine
2-(trans-4-pentylcyclohexyl)-5-[2-(p-cyanophenyl)-ethyl]-pyrimidine
2-(trans-4-pentylcyclohexyl)-5-[2-(p-methoxyphenyl)-ethyl]-pyrimidine
2-(trans-4-pentylcyclohexyl)-5-[2-(p-propoxyphenyl)-ethyl]-pyrimidine
2-(trans-4-pentylcyclohexyl)-5-[2-(p-pentoxyphenyl)-ethyl]-pyrimidine
2-(trans-4-pentylcyclohexyl)-5-[2-(p-heptoxyphenyl)-ethyl]-pyrimidine
2-(trans-4-pentylcyclohexyl)-5-[2-(p-nonoxyphenyl)-ethyl]-pyrimidine
2-(trans-4-pentylcyclohexyl)-5-[2-(p-decoxyphenyl)-ethyl]-pyrimidine
2-(trans-4-pentylcyclohexyl)-5-[2-(p-dodecoxyphenyl)-ethyl]-pyrimidine
2-(trans-4-pentylcyclohexyl)-5-[2-(p-ethylphenyl)-ethyl]-pyrimidine
2-(trans-4-pentylcyclohexyl)-5-[2-(p-propylphenyl)-ethyl]-pyrimidine
2-(trans-4-pentylcyclohexyl)-5-[2-(p-butylphenyl)-ethyl]-pyrimidine
2-(trans-4-pentylcyclohexyl)-5-[2-(p-pentylphenyl)-ethyl]-pyrimidine
2-(trans-4-pentylcyclohexyl)-5-[2-(p-heptylphenyl)-ethyl]-pyrimidine
2-(trans-4-pentylcyclohexyl)-5-[2-(p-nonylphenyl)-ethyl]-pyrimidine.

EXAMPLE 3

2-(trans-4-Propylcyclohexyl)-5-(2-oxapentyl)-pyrimidine is prepared in the manner described in Example 1, starting from trans-4-pentylcyclohexyl-carbonitrile.

The following compounds are prepared analogously:
2-(trans-4-propylcyclohexyl)-5-(2-oxapropyl)-pyrimidine
2-(trans-4-propylcyclohexyl)-5-(2-oxabutyl)-pyrimidine
2-(trans-4-propylcyclohexyl)-5-(2-oxapentyl)-pyrimidine
2-(trans-4-propylcyclohexyl)-5-(2-oxahexyl)-pyrimidine
2-(trans-4-butylcyclohexyl)-5-(2-oxapropyl)-pyrimidine
2-(trans-4-butylcyclohexyl)-5-(2-oxabutyl)-pyrimidine
2-(trans-4-butylcyclohexyl)-5-(2-oxapentyl)-pyrimidine
2-(trans-4-butylcyclohexyl)-5-(2-oxahexyl)-pyrimidine
2-(trans-4-butylcyclohexyl)-5-(2-oxaheptyl)-pyrimidine
2-(trans-4-butylcyclohexyl)-5-(2-oxaoctyl)-pyrimidine
2-(trans-4-pentylcyclohexyl)-5-(2-oxapropyl)-pyrimidine
2-(trans-4-pentylcyclohexyl)-5-(2-oxabutyl)-pyrimidine 2-(trans-4-pentylcyclohexyl)-5-(2-oxapentyl)-pyrimidine
2-(trans-4-pentylcyclohexyl)-5-(2-oxahexyl)-pyrimidine
2-(trans-4-pentylcyclohexyl)-5-(2-oxaheptyl)-pyrimidine
2-(trans-4-pentylcyclohexyl)-5-(2-oxaoctyl)-pyrimidine
2-(trans-4-heptylcyclohexyl)-5-(2-oxapropyl)-pyrimidine
2-(trans-4-heptylcyclohexyl)-5-(2-oxabutyl)-pyrimidine
2-(trans-4-heptylcyclohexyl)-5-(2-oxapentyl)-pyrimidine
2-(trans-4-heptylcyclohexyl)-5-(2-oxahexyl)-pyrimidine
2-(trans-4-heptylcyclohexyl)-5-(2-oxaheptyl)-pyrimidine
2-(trans-4-heptylcyclohexyl)-5-(2-oxaoctyl)-pyrimidine.

EXAMPLE 4

28 g of diethyl trans-4-propylcyclohexyl-malonate and a suspension of 20 g of 4-ethoxy-benzocarboximideamide hydrochloride in 50 ml of ethanol are added in succession to a sodium ethanolate solution prepared from 6.9 g of sodium and 200 ml of ethanol. After the reaction mixture has been stirred for 8 hours, it is poured into 500 ml of ice-water and neutralized with dilute hydrochloric acid. Extraction with several portions of methylene chloride and subsequent removal of the solvent by distillation gives a residue, which is recrystallised twice from ethanol. Yield: 23 g of 4,6-dihydroxy-2-(4-ethoxyphenyl)-5-(trans-4-propylcyclohexyl)-pyrimidine.

22 g of the dihydropyrimidine are heated under reflux with 19 g of N,N-diethylaniline and 80 ml of phosphorus oxytrichloride for 48 hours. The cooled reaction solution is poured onto ice. After extraction with methylene chloride and subsequent removal of the solvent by distillation, the residue which remains, consisting of 4,6-dichloro-2-(4-ethoxyphenyl)-5-(trans-4-propylcyclohexyl)-pyrimidine, is dissolved in 300 ml of methanol and, after addition of palladium-on-charcoal (5% of Pd) is hydrogenated at room temperature. The catalyst is removed by filtration, the solvent is distilled off and the residue is subjected to separation by column chromatography (silica gel/toluene). 2-(4-Ethoxyphenyl)-5-(trans-4-propylcyclohexyl)-pyrimidine is obtained from the main fraction, after removal of the solvent and customary working up.

The following compounds are prepared analogously:
2-(4-ethoxyphenyl)-5-(trans-4-ethylcyclohexyl)-pyrimidine
2-(4-ethoxyphenyl)-5-(trans-4-butylcyclohexyl)-pyrimidine
2-(4-ethoxyphenyl)-5-(trans-4-pentylcyclohexyl)-pyrimidine
2-(4-ethoxyphenyl)-5-(trans-4-heptylcyclohexyl)-pyrimidine
2-(4-methoxyphenyl)-5-(trans-4-ethylcyclohexyl)-pyrimidine
2-(4-methoxyphenyl)-5-(trans-4-propylcyclohexyl)-pyrimidine
2-(4-methoxyphenyl)-5-(trans-4-butylcyclohexyl)-pyrimidine
2-(4-methoxyphenyl)-5-(trans-4-pentylcyclohexyl)-pyrimidine
2-(4-methoxyphenyl)-5-(trans-4-heptylcyclohexyl)-pyrimidine
2-(4-propoxyphenyl)-5-(trans-4-ethylcyclohexyl)-pyrimidine
2-(4-propoxyphenyl)-5-(trans-4-propylcyclohexyl)-pyrimidine
2-(4-propoxyphenyl)-5-(trans-4-butylcyclohexyl)-pyrimidine
2-(4-propoxyphenyl)-5-(trans-4-pentylcyclohexyl)-pyrimidine
2-(4-propoxyphenyl)-5-(trans-4-heptylcyclohexyl)-pyrimidine
2-(4-butoxyphenyl)-5-(trans-4-ethylcyclohexyl)-pyrimidine
2-(4-butoxyphenyl)-5-(trans-4-propylcyclohexyl)-pyrimidine
2-(4-butoxyphenyl)-5-(trans-4-butylcyclohexyl)-pyrimidine
2-(4-butoxyphenyl)-5-(trans-4-pentylcyclohexyl)-pyrimidine
2-(4-butoxyphenyl)-5-(trans-4-hexylcyclohexyl)-pyrimidine, m.p. 75°, c.p. 196°
2-(4-butoxyphenyl)-5-(trans-4-heptylcyclohexyl)-pyrimidine
2-(4-pentoxyphenyl)-5-(trans-4-ethylcyclohexyl)-pyrimidine
2-(4-pentoxyphenyl)-5-(trans-4-propylcyclohexyl)-pyrimidine
2-(4-pentoxyphenyl)-5-(trans-4-butylcyclohexyl)-pyrimidine
2-(4-pentoxyphenyl)-5-(trans-4-pentylcyclohexyl)-pyrimidine
2-(4-pentoxyphenyl)-5-(trans-4-heptylcyclohexyl)-pyrimidine
2-(4-hexoxyphenyl)-5-(trans-4-ethylcyclohexyl)-pyrimidine
2-(4-hexoxyphenyl)-5-(trans-4-propylcyclohexyl)-pyrimidine
2-(4-hexoxyphenyl)-5-(trans-4-butylcyclohexyl)-pyrimidine
2-(4-hexoxyphenyl)-5-(trans-4-pentylcyclohexyl)-pyrimidine
2-(4-hexoxyphenyl)-5-(trans-4-heptylcyclohexyl)-pyrimidine
2-(4-heptoxyphenyl)-5-(trans-4-ethylcyclohexyl)-pyrimidine
2-(4-heptoxyphenyl)-5-(trans-4-propylcyclohexyl)-pyrimidine
2-(4-heptoxyphenyl)-5-(trans-4-butylcyclohexyl)-pyrimidine
2-(4-heptoxyphenyl)-5-(trans-4-pentylcyclohexyl)-pyrimidine
2-(4-heptoxyphenyl)-5-(trans-4-heptylcyclohexyl)-pyrimidine
2-(4-nonoxyphenyl)-5-(trans-4-ethylcyclohexyl)-pyrimidine
2-(4-nonoxyphenyl)-5-(trans-4-propylcyclohexyl)-pyrimidine
2-(4-nonoxyphenyl)-5-(trans-4-butylcyclohexyl)-pyrimidine
2-(4-nonoxyphenyl)-5-(trans-4-pentylcyclohexyl)-pyrimidine
2-(4-nonoxyphenyl)-5-(trans-4-heptylcyclohexyl)-pyrimidine
2-(4-undecoxyphenyl)-5-(trans-4-ethylcyclohexyl)-pyrimidine
2-(4-undecoxyphenyl)-5-(trans-4-propylcyclohexyl)-pyrimidine
2-(4-undecoxyphenyl)-5-(trans-4-butylcyclohexyl)-pyrimidine
2-(4-undecoxyphenyl)-5-(trans-4-pentylcyclohexyl)-pyrimidine 2-(4-undecoxyphenyl)-5-(trans-4-heptylcyclohexyl)-pyrimidine
2-(4-dodecoxyphenyl)-5-(trans-4-ethylcyclohexyl)-pyrimidine
2-(4-dodecoxyphenyl)-5-(trans-4-propylcyclohexyl)-pyrimidine
2-(4-dodecoxyphenyl)-5-(trans-4-butylcyclohexyl)-pyrimidine
2-(4-dodecoxyphenyl)-5-(trans-4-pentylcyclohexyl)-pyrimidine
2-(4-dodecoxyphenyl)-5-(trans-4-heptylcyclohexyl)-pyrimidine.

EXAMPLE 5

A mixture of 11 g of 2-p-hydroxyphenyl-5-n-hexyl-pyrimidine, 7.8 g of trans-4-n-propyl-1-bromomethylcyclohexane, 8.6 g of potassium carbonate and 50 ml of dimethylformamide is warmed at 90° for 10 hours. Customary working up gives 4-(5-n-hexylpyrimidin-2-yl)-phenyl trans-4-n-propylcyclohexylmethyl ether.

The following compounds are prepared analogously:
4-(5-hexylpyrimidin-2-yl)-phenyl trans-4-ethylcyclohexylmethyl ether
4-(5-hexylpyrimidin-2-yl)-phenyl trans-4-butylcyclohexylmethyl ether
4-(5-hexylpyrimidin-2-yl)-phenyl trans-4-pentylcyclohexylmethyl ether, m.p. 99°, c.p. 150°
4-(5-hexylpyrimidin-2-yl)-phenyl trans-4-heptylcyclohexylmethyl ether
4-(5-heptylpyrimidin-2-yl)-phenyl trans-4-ethylcyclohexylmethyl ether
4-(5-heptylpyrimidin-2-yl)-phenyl trans-4-propylcyclohexylmethyl ether
4-(5-heptylpyrimidin-2-yl)-phenyl trans-4-butylcyclohexylmethyl ether
4-(5-heptylpyrimidin-2-yl)-phenyl trans-4-pentylcyclohexylmethyl ether
4-(5-heptylpyrimidin-2-yl)-phenyl trans-4-heptylcyclohexylmethyl ether
4-(5-nonylpyrimidin-2-yl)-phenyl trans-4-ethylcyclohexylmethyl ether
4-(5-nonylpyrimidin-2-yl)-phenyl trans-4-propylcyclohexylmethyl ether
4-(5-nonylpyrimidin-2-yl)-phenyl trans-4-butylcyclohexylmethyl ether
4-(5-nonylpyrimidin-2-yl)-phenyl trans-4-pentylcyclohexylmethyl ether
4-(5-nonylpyrimidin-2-yl)-phenyl trans-4-heptylcyclohexylmethyl ether
4-(5-pentylpyrimidin-2-yl)-phenyl trans-4-ethylcyclohexylmethyl ether
4-(5-pentylpyrimidin-2-yl)-phenyl trans-4-propylcyclohexylmethyl ether
4-(5-pentylpyrimidin-2-yl)-phenyl trans-4-butylcyclohexylmethyl ether
4-(5-pentylpyrimidin-2-yl)-phenyl trans-4-pentylcyclohexylmethyl ether
4-(5-pentylpyrimidin-2-yl)-phenyl trans-4-heptylcyclohexylmethyl ether
4-(5-propylpyrimidin-2-yl)-phenyl trans-4-ethylcyclohexylmethyl ether
4-(5-propylpyrimidin-2-yl)-phenyl trans-4-propylcyclohexylmethyl ether
4-(5-propylpyrimidin-2-yl)-phenyl trans-4-butylcyclohexylmethyl ether
4-(5-propylpyrimidin-2-yl)-phenyl trans-4-pentylcyclohexylmethyl ether
4-(5-propylpyrimidin-2-yl)-phenyl trans-4-heptylcyclohexylmethyl ether.

The following examples relate to liquid crystal phases according to the invention:

EXAMPLE A

A liquid crystal phase is prepared from
17% of p-trans-4-propylcyclohexyl-benzonitrile,
23% of p-trans-4-pentylcyclohexyl-benzonitrile,
16% of trans-1-p-ethoxyphenyl-4-propylcyclohexane,
14% of trans-1-p-butoxyphenyl-4-propylcyclohexane,
10% of 4-(trans-4-pentylcyclohexyl)-4'-(trans-4-propylcyclohexyl)-biphenyl,
10% of 2-(4-ethoxyphenyl)-5-(trans-4-propylcyclohexyl)-pyrimidine and
10% of 2-(4-methoxyphenyl)-5-(trans-4-pentylcyclohexyl)-pyrimidine.

EXAMPLE B

A liquid crystal phase is prepared from
21% of p-trans-4-ethylcyclohexyl-benzonitrile,
22% of p-trans-4-butylcyclohexyl-benzonitrile,
14% of 4-ethyl-4'-cyanobiphenyl,
18% of 4-butyl-4'-cyanobiphenyl,
10% of p-pentylphenyl 2-(trans-4-propylcyclohexyl)-pyrimidine-5-carboxylate and
15% of 2-[trans-4-(trans-5-propyl-1,3-dioxan-2-yl)-cyclohexyl]-5-pentylpyrimidine.

EXAMPLE C

A liquid crystal phase consisting of
8% of 2-p-cyanophenyl-5-butyl-1,3-dioxane,
7% of 2-p-cyanophenyl-5-pentyl-1,3-dioxane,
8% of 4-cyano-4'-(trans-4-pentylcyclohexyl)-biphenyl,
5% of 4-ethyl-4'-(trans-4-pentylcyclohexyl)-biphenyl,
5% of 2-(4-ethoxyphenyl)-5-(trans-4-propylcyclohexyl)-pyrimidine,
5% of 2-p-pentoxyphenyl-5-hexylpyrimidine,
5% of 2-p-hexoxyphenyl-5-hexylpyrimidine,
6% of 2-p-heptoxyphenyl-5-hexylpyrimidine,
8% of 2-p-nonoxyphenyl-5-hexylpyrimidine,
8% of 2-p-undecoxyphenyl-5-hexylpyrimidine,
7% of p-methoxyphenyl trans-4-propylcyclohexanecarboxylate,
7% of p-ethoxyphenyl trans-4-propylcyclohexanecarboxylate,
7% of p-methoxyphenyl trans-4-butylcyclohexanecarboxylate,
7% of p-ethoxyphenyl trans-4-butylcyclohexanecarboxylate and
7% of p-methoxyphenyl trans-4-pentylcyclohexanecarboxylate has a viscosity of $49 \times 10^{-3}$ Pa.s and is particularly suitable for liquid crystal display elements of high multiplexing capacity.

EXAMPLE D

A liquid crystal phase consisting of
8.0% of trans-1-p-propylphenyl-4-pentylcyclohexane,
7.0% of 2-p-cyanophenyl-5-propyl-1,3-dioxane,
8.0% of 2-p-cyanophenyl-5-butyl-1,3-dioxane,
7.0% of 2-p-cyanophenyl-5-pentyl-1,3-dioxane,
7.5% of 4-cyano-4'-(trans-4-pentylcyclohexyl)-biphenyl,
5.0% of 4-ethyl-4'-(trans-4-pentylcyclohexyl)-biphenyl,
5.0% of 4-ethyl-4'-(trans-4-propylcyclohexyl)-biphenyl,
5.0% of 2-p-pentoxyphenyl-5-hexylpyrimidine,
5.0% of 2-hexoxyphenyl-5-hexylpyrimidine, 6.0% of 2-p-heptoxyphenyl-5-hexylpyrimidine,
8.0% of 2-p-nonoxyphenyl-5-hexylpyrimidine,
8.0% of 2-p-undecoxyphenyl-5-hexylpyrimidine,
0.5% of 2-(trans,trans-4'-butyl-bicyclohex-4-yl)-5-pentylpyrimidine,
7.0% of p-methoxyphenyl trans-4-propylcyclohexanecarboxylate,
7.0% of p-ethoxyphenyl trans-4-propylcyclohexanecarboxylate and
6.0% of p-methoxyphenyl trans-4-butylcyclohexanecarboxylate
has a clear point of 64° and a viscosity of $45 \times 10^{-3}$ Pa.s and is particularly suitable for liquid crystal display elements of high multiplexing capacity.

EXAMPLE E

A liquid crystal phase consisting of
7% of 2-p-cyanophenyl-5-propyl-1,3-dioxane,
6% of 2-p-cyanophenyl-5-butyl-1,3-dioxane,
5% of 2-p-cyanophenyl-5-pentyl-1,3-dioxane,
4% of 2-p-pentoxyphenyl-5-hexylpyrimidine,
4% of 2-p-hexoxyphenyl-5-hexylpyrimidine,
5% of 2-p-heptoxyphenyl-5-hexylpyrimidine,
7% of 2-p-nonoxyphenyl-5-hexylpyrimidine,
7% of 2-p-undecoxyphenyl-5-hexylpyrimidine,
6% of p-methoxyphenyl trans-4-propylcyclohexanecarboxylate,
4% of p-methoxyphenyl trans-4-butylcyclohexanecarboxylate,
3% of p-methoxyphenyl trans-4-pentylcyclohexanecarboxylate,
9% of trans-1-p-propylphenyl-4-pentylcyclohexane,
3% of p-trans-4-propylcyclohexyl-phenyl butyrate,
18% of 2-(trans,trans-4'-butyl-bicyclohex-4-yl)-5-pentylpyrimidine,
9% of 2-[4-(2-trans-4-propylcyclohexylethyl)-phenyl]-5-pentylpyrimidine and
3% of 2-[4-(2-trans-4-propylcyclohexylethyl)-phenyl]-5-heptylpyrimidine
is particularly suitable for liquid crystal display elements of high multiplexing capacity.

EXAMPLE F

A liquid crystal phase consisting of
3% of 2-p-cyanophenyl-5-pentyl-1,3-dioxane,
6% of 4-cyano-4'-(trans-4-pentylcyclohexyl)-biphenyl,
7% of 2-[4-(2-trans-4-propylcyclohexylethyl)-phenyl]-5-pentylpyrimidine,
8% of 2-[4-(2-trans-4-propylcyclohexylethyl)-phenyl]-5-heptylpyrimidine,
5% of 2-p-octoxyphenyl-5-pentylpyrimidine,
5% of 2-p-pentoxyphenyl-5-hexylpyrimidine,
5% of 2-p-heptoxyphenyl-5-hexylpyrimidine,
4% of 2-p-nonoxyphenyl-5-hexylpyrimidine,
5% of 2-p-heptoxyphenyl-5-heptylpyrimidine,
4% of 2-p-nonoxyphenyl-5-heptylpyrimidine,
5% of 2-p-nonoxyphenyl-5-nonylpyrimidine,
5% of p-methoxyphenyl trans-4-propylcyclohexanecarboxylate,
7% of p-methoxyphenyl trans-4-butylcyclohexanecarboxylate,
8% of p-methoxyphenyl trans-4-pentylcyclohexanecarboxylate,
17% of trans-1-p-propylphenyl-4-pentylcyclohexane and
6% of p-trans-4-propylcyclohexyl-phenyl butyrate
has a clear point of 65°. This mixture is particularly suitable for liquid crystal display elements of high multiplexing capacity.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and without departing from the spirit and scope thereof, can make various changes and modifications of the invention to adapt it to various usages and conditions.

What is claimed is:

1. In a liquid crystalline phase comprising at least two liquid crystalline compounds, the improvement wherein at least one compound is of the formula Iaa

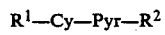

$$R^1\text{—Cy—Pyr—}R^2 \qquad \text{Iaa}$$

wherein
$R^1$ is straight chain alkyl with 1–15 C atoms,
$R^2$ is straight chain alkyl with 1–15 C atoms,
  wherein one or two nonadjacent CH$_2$ groups are replaced by —O—,
Cy is a 1,4-cyclohexylene group and
Pyr is a pyrimidine-2,5-diyl group.

2. A phase of claim 1 wherein $R^1$, Pyr and Cy have the meaning given and
$R^2$ is methoxy, ethoxy, propoxy, butoxy, pentoxy, hexoxy, heptoxy, octoxy, nonoxy, decoxy, 2-oxapropyl, 2- or 3-oxabutyl, 2-, 3-, or 4-oxapentyl, 2-, 3-, 4- or 5-oxahexyl, 2-, 3-, 4-, 5-, or 6-oxyaheptyl, 2-, 3-, 4-, 5-, 6- or 7-oxaoctyl, 2-, 3-, 4-, 5-, 6-, 7-, or 8-oxanonyl, 2-, 3-, 4-, 5-, 6-, 7-, 8- or 9-oxadecyl, 1,3-dioxabutyl, 1,3-, 1,4-, or 2,-dioxapentyl, 1,3-, 1,4-, 1,5-, 2,4-, 2,5-, or 3,6 dioxahexyl, 1,3-, 1,4-, 1,5-, 1,6-, 2,4-, 2,5-, 2,6-, 3,5-, 3,6- or 4,6-dioxaheptyl.

3. A phase of claim 1 wherein said compound is of formula Iaa'

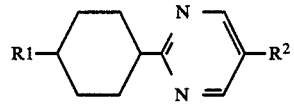

wherein $R^1$ and $R^2$ have the meaning given in claim 1.

4. A phase of claim 3 wherein $R^1$ has the meaning given and $R^2$ is methoxy, ethoxy, propoxy, butoxy, pentoxy, hexoxy, heptoxy, octoxy, nonoxy, decoxy, 2-oxapropyl, 2- or 3-oxabutyl, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2, 3-, 4-, 5-, 6-, 7- or 8-oxanonyl, 2-, 3-, 4-, 5-, 6-, 7-, 8- or 9-oxadecyl.

5. In a liquid crystal display element comprising a liquid crystalline phase the improvement wherein the phase is one of claim 1.

6. In an electrooptical display element comprising a liquid crystalline dielectric, the improvement wherein the dielectric is a phase of claim 1.

* * * * *

UNITED STATES PATENT AND TRADEMARK OFFICE
CERTIFICATE OF CORRECTION

PATENT NO. : 4,882,082

DATED : November 21, 1989

INVENTOR(S) : RUDOLF EIDENSCHINK ET AL

It is certified that error appears in the above-identified patent and that said Letters Patent is hereby corrected as shown below:

Column 32, claim 2, line 39:

reads "1,3-dioxabutyl, 1,3-, 1,4-, or 2,-dioxapentyl, 1,3-,"

should read -- 1,3-dioxabutyl, 1,3-, 1,4-, or 2,4-dioxapentyl, 1,3-, --

Signed and Sealed this

Twenty-ninth Day of January, 1991

Attest:

HARRY F. MANBECK, JR.

*Attesting Officer*      *Commissioner of Patents and Trademarks*